US008497106B2

(12) United States Patent  
Suarez

(10) Patent No.: US 8,497,106 B2  
(45) Date of Patent: Jul. 30, 2013

(54) IMMOBILISATION OF BIOLOGICAL MOLECULES

(75) Inventor: Guillaume Suarez, Tyneside (GB)

(73) Assignee: The University of Newcastle, Tyneside (GB)

( * ) Notice: Subject to any disclaimer, the term of this patent is extended or adjusted under 35 U.S.C. 154(b) by 894 days.

(21) Appl. No.: 11/993,012

(22) PCT Filed: Jul. 6, 2006

(86) PCT No.: PCT/GB2006/002510  
§ 371 (c)(1),  
(2), (4) Date: Nov. 18, 2009

(87) PCT Pub. No.: WO2007/007052  
PCT Pub. Date: Jan. 18, 2007

(65) Prior Publication Data  
US 2010/0285561 A1    Nov. 11, 2010

(30) Foreign Application Priority Data  
Jul. 7, 2005    (GB) .................................. 0513910.0

(51) Int. Cl.  
C12N 11/14    (2006.01)  
B05D 3/10    (2006.01)  
H01L 21/02    (2006.01)

(52) U.S. Cl.  
USPC .......... 435/176; 427/2.13; 436/149; 436/501; 436/514

(58) Field of Classification Search  
None  
See application file for complete search history.

(56) References Cited

U.S. PATENT DOCUMENTS

| 4,148,689 | A | 4/1979 | Hino et al. |
| 5,494,815 | A | 2/1996 | Von Gentzkow et al. |
| 2002/0090738 | A1 | 7/2002 | Cozzette et al. |
| 2002/0155481 | A1 | 10/2002 | Hirota et al. |
| 2003/0207468 | A1 | 11/2003 | Coyne et al. |
| 2003/0219597 | A1 | 11/2003 | Carr et al. |
| 2004/0043508 | A1 | 3/2004 | Frutos et al. |
| 2004/0096849 | A1 | 5/2004 | Klapproth et al. |
| 2004/0121399 | A1 | 6/2004 | Brock et al. |
| 2005/0003743 | A1* | 1/2005 | Minamihaba et al. .......... 451/41 |
| 2005/0037276 | A1 | 2/2005 | Argitis et al. |
| 2006/0134672 | A1 | 6/2006 | Chang et al. |

FOREIGN PATENT DOCUMENTS

| EP | 0 643 305 A2 | 3/1995 |
| EP | 1 265 071 A2 | 12/2002 |
| EP | 1 291 655 | 12/2003 |
| JP | 07-151759 | 6/1995 |
| JP | 10-267930 A | 10/1998 |
| JP | 25-36955 B2 | 2/1999 |
| JP | 11-242031 A | 9/1999 |
| JP | 11-264819 A | 9/1999 |
| JP | 2003-014743 A | 1/2003 |
| JP | 2003-014745 | 1/2003 |
| JP | 2003-177129 A | 6/2003 |
| JP | 2004-286728 A | 10/2004 |
| JP | 2005-118049 A | 5/2005 |
| WO | WO 02/37110 A1 | 5/2002 |
| WO | WO 02/063264 | 8/2002 |
| WO | WO 02/063310 A1 | 8/2002 |
| WO | WO 03/000433 A1 | 1/2003 |
| WO | WO 03/093785 A2 | 11/2003 |
| WO | WO 2004/011672 | 2/2004 |
| WO | WO2005/014745 | 2/2005 |
| WO | WO 2007/069608 A1 | 6/2007 |

OTHER PUBLICATIONS

Blawas, et al., "Protein Patterning," Biomaterials 1998, vol. 19, 595-609.  
Britland, S., et al., "Micropatterning Proteins and Synthetic Peptides on Solid Supports: A Novel Application for Microelectronics Fabrication Technology," Biotechnol. Prog. 1992, 8, 155-160.  
Heiney, P., et al., "Structure and Growth of Chromophore-Functionalized (3-Aminoproply) Triethoxysilane Self-Assembled on Silicon," Langmuir 2000, 16, 2651-2657.  
Kane, et al., "Patterning Proteins and Cells Using Soft Lithography," Biomaterials 1999, vol. 20, 2363-2376.  
Salloum, et al., "Protein Adsorption Modalities on Polyelectrolyte Multilayers," Biomacromolecules 2004, vol. 5, 1089-1096.  
Sorribas, et al., "Photolithographic Generation of Protein Micropatterns for Neuron Culture Applications," Biomaterials 2002, vol. 23, 893-900.  
Tanii, et al., "Preferential Immobilization of Biomolecules on Silicon Microstructure Array by Means of Electron Beam Lithography on Organosilane Self-Assembled Monolayer Resist," Applied Surface Science, vol. 234, 102-106, Jun. 19, 2004.  
Vandenberg, et al., "Structure of 3-Aminoproply Triethoxy Silane on Silicon Oxide," J. Colloids and Interf. Sc. 1991, vol. 147, 103-118.  
Wang, Z.H., et al., "Silicon Surface Modification with a Mixed Silanes Layer to Immobilize Proteins for Biosensor with Imaging Ellipsometry," Colloids & Surfaces B, 2004 34, 173-177.  
Weiping, Q. et al., "Controlled Site-Directed Assembly of Antibodies by Their Oligosaccharide Moieties onto APTES Derivatized Surfaces," J. Colloids & Interf. Sc. 1999, 214, 16-19.  
Weiping, Q., et al., "Site-directed Immobilization of Immunoglobulin G on 3-Aminopropyltriethoxylsilane Modified Silicon Wafer Surfaces," Mat. Sc. & Engin. C 1999, 8-9, 475-480.  
Wieringa, R.H., "The Aminosilane Coupling Layer," Thesis, University of Groningen, Dec. 2000, Chap 2.

(Continued)

*Primary Examiner* — Lisa J Hobbs  
(74) *Attorney, Agent, or Firm* — Knobbe, Martens, Olson & Bear LLP

(57) ABSTRACT

A method of immobilising a biological molecule on a substrate comprises: (i) covalently attaching a substantially three-dimensional polysilane polymer to a substrate; and (ii) attaching a biological molecule onto and/or within the polymer. The method may additionally comprise the steps of coating the substrate (or the chemically protective layer) with a layer of radiation sensitive material, exposing the substrate to a source of radiation, and incubating the substrate in the presence of a first species of biological molecule.

44 Claims, 9 Drawing Sheets

OTHER PUBLICATIONS

Wilson, et al., "Functional Protein Microarrays," Curr. Op. Chem. Biol. 2001, vol. 6, 81-85.

Zhang, C.X., et al., "Protein Microarray—A New Tool for Detection of TORCH Infections," 8th International Conference of Electronic Materials (IUMRS-ICEM) 2002, Xi'an China.

Zhang, G.J., et al., "The Immobilization of DNA on Microstructured Patterns Fabricated by Maskless Lithography," Sens. Actuat. B 2004, 97, 243-248.

Zheng, J., et al., "Nanopatterned Assembling of Colloidal Gold Nanoparticles on Silicon," Langmuir 2000, 16, 4409-4412.

* cited by examiner

Figure:1
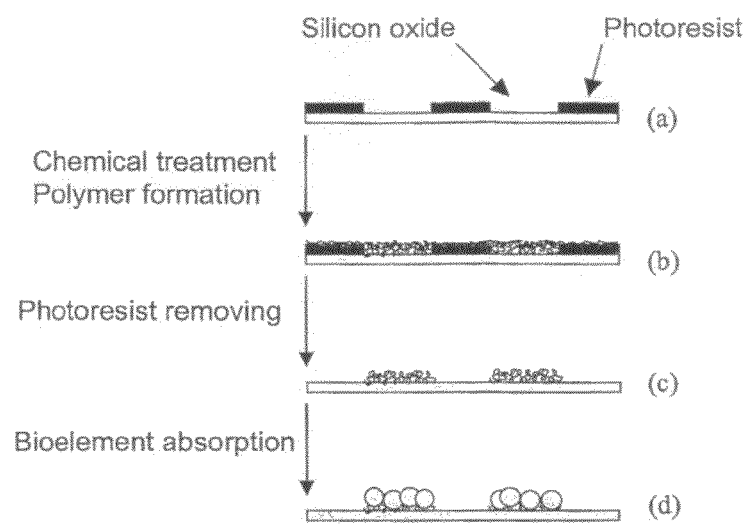
Figure:2
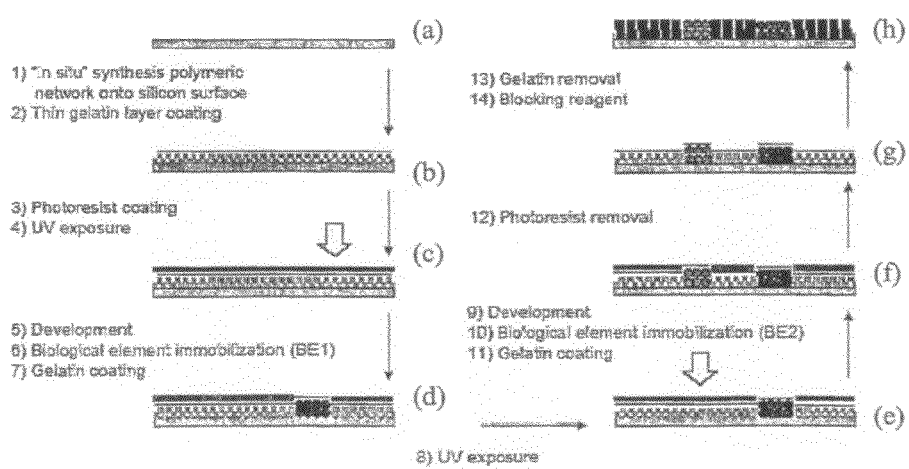

Figure: 3
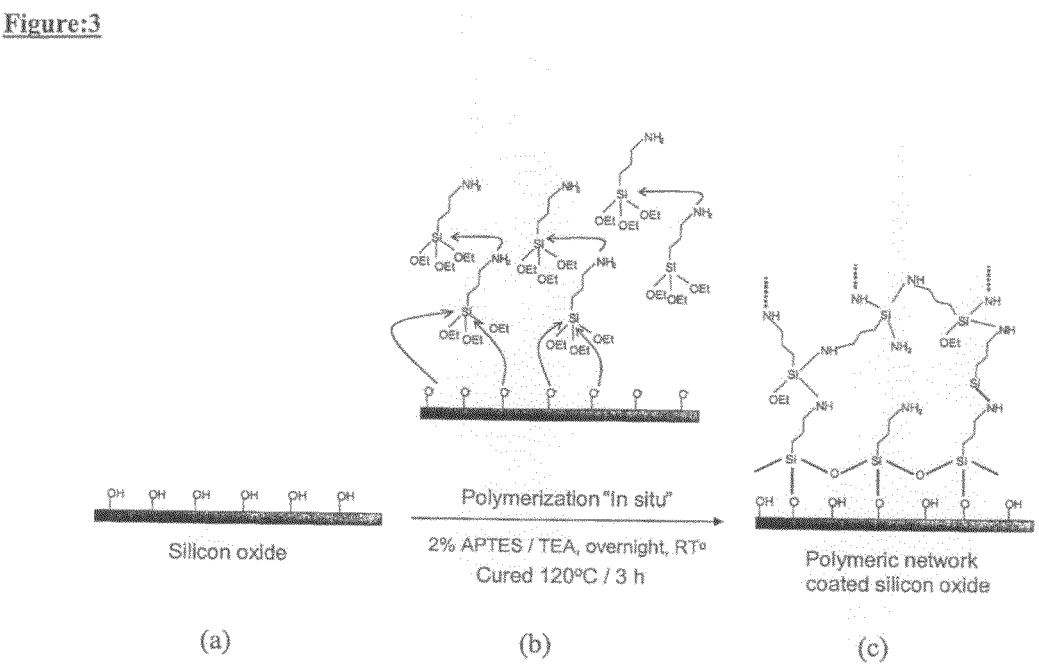
Figure: 4
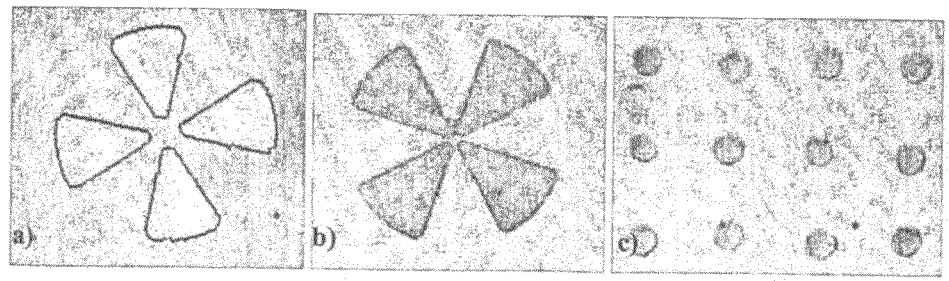

Figure: 5
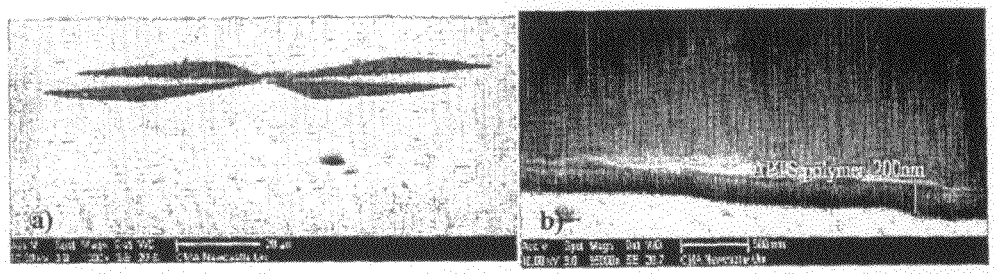
Figure: 6
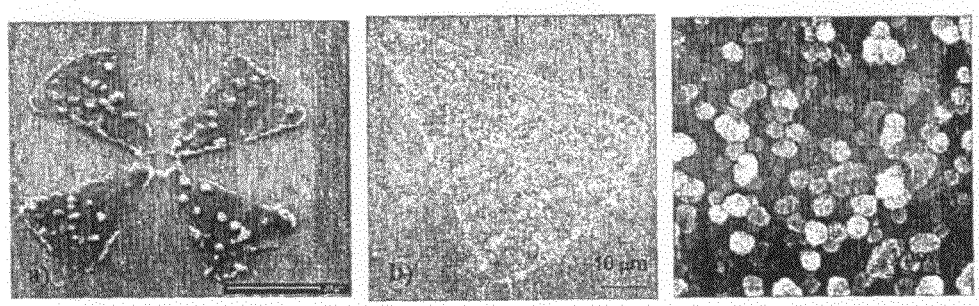
Figure: 7
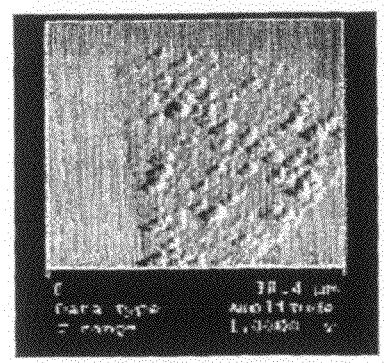

Figure:8
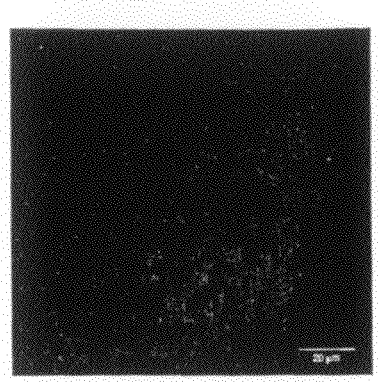
Figure:9
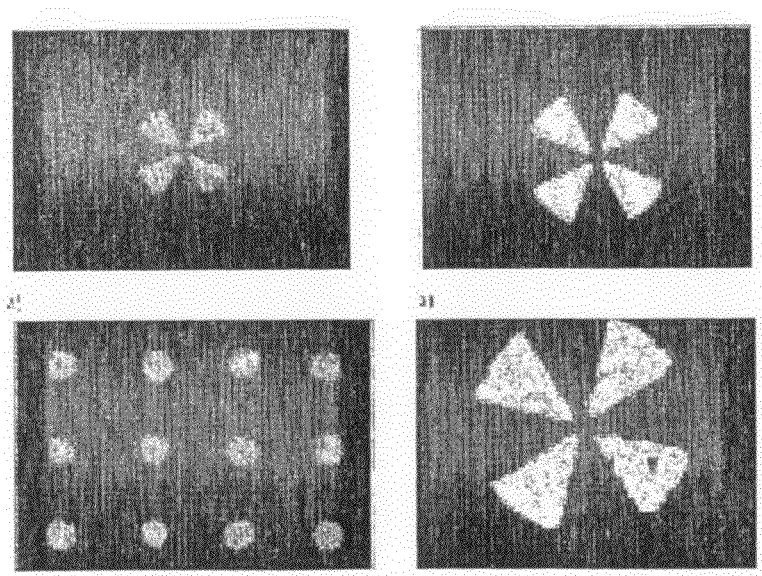

Figure:10
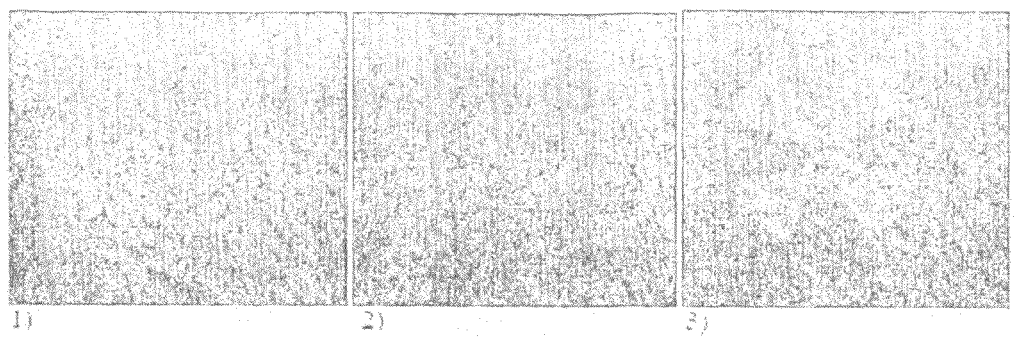
Figure:11
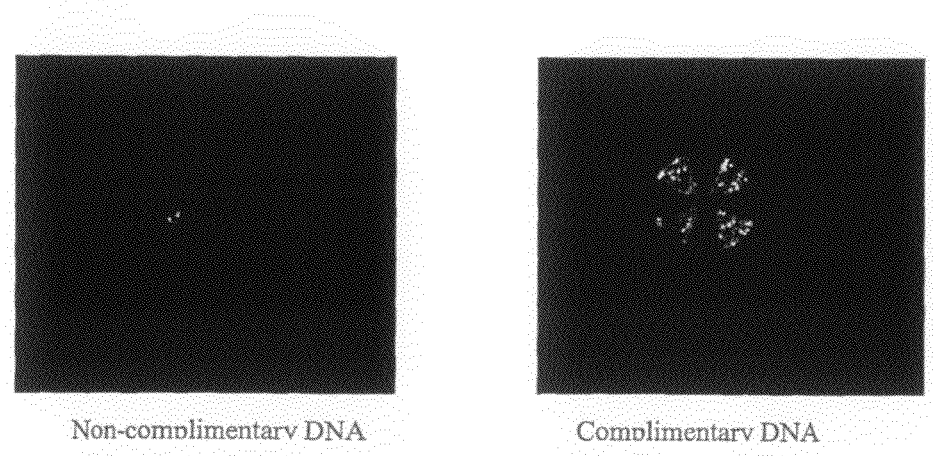
Non-complimentary DNA       Complimentary DNA Figure: 12
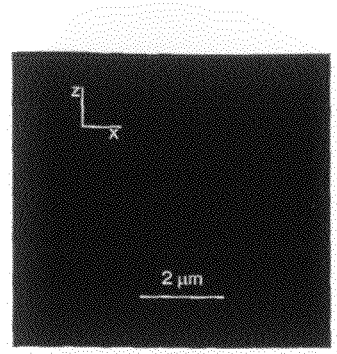
Figure: 13
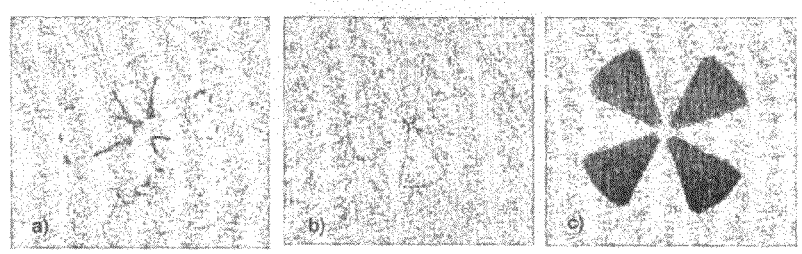
Figure: 14
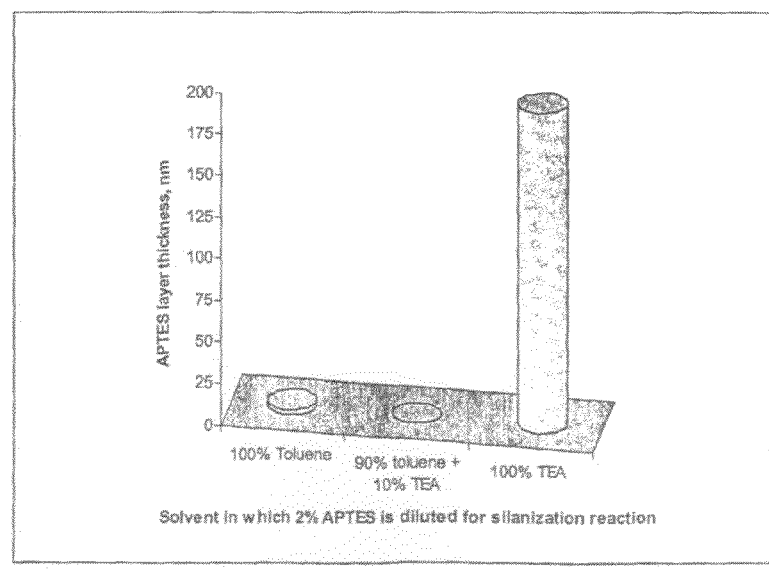

Figure:15
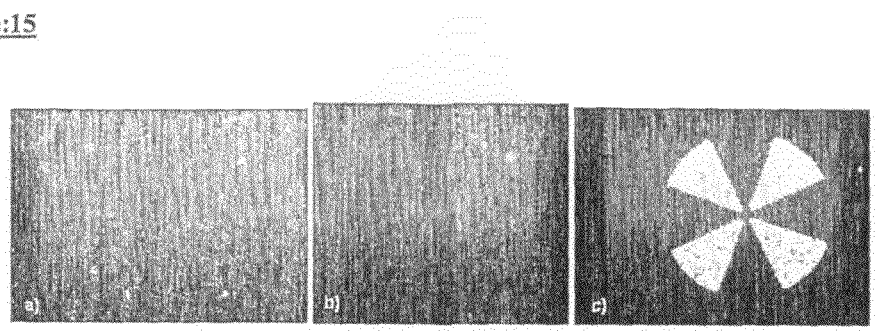
Figure:16
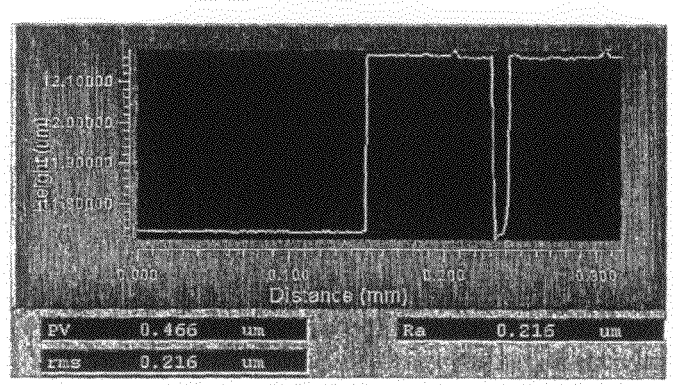

Figure:17
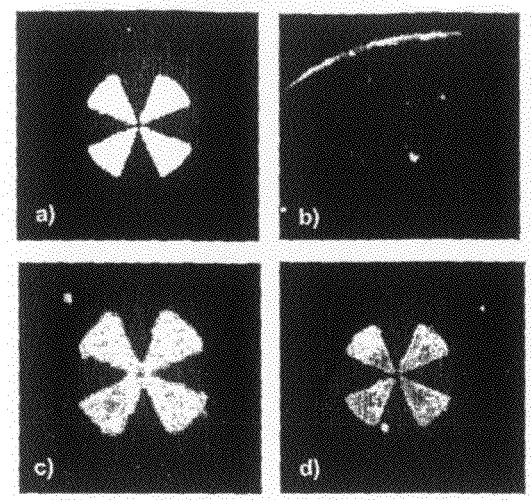
Figure:18
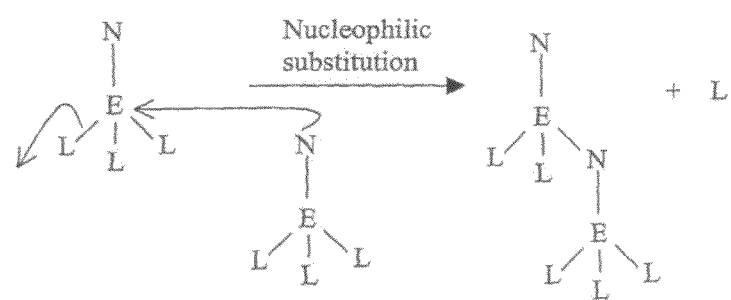

Figure: 19
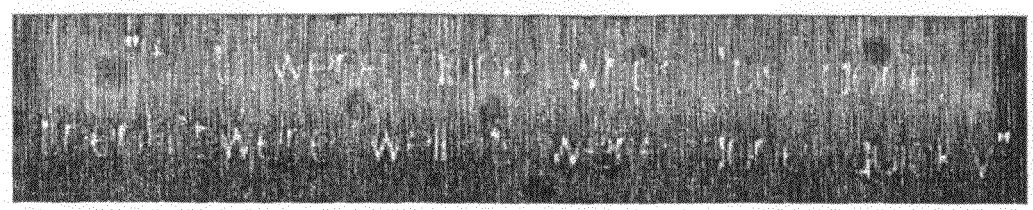
A- Sentence patterned (200 nm lines) in an e-beam sensitive material (PMMA) coated onto silicon.
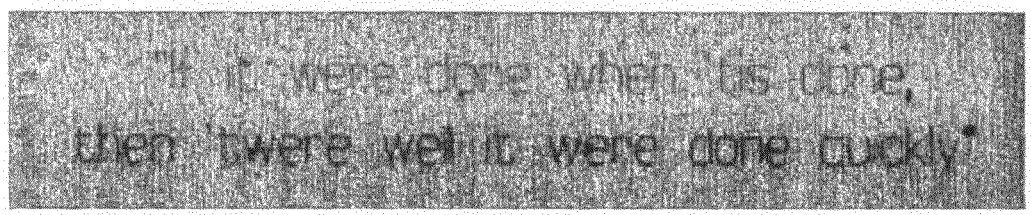
B- Polymeric network patterned after chemical treatment of the surface
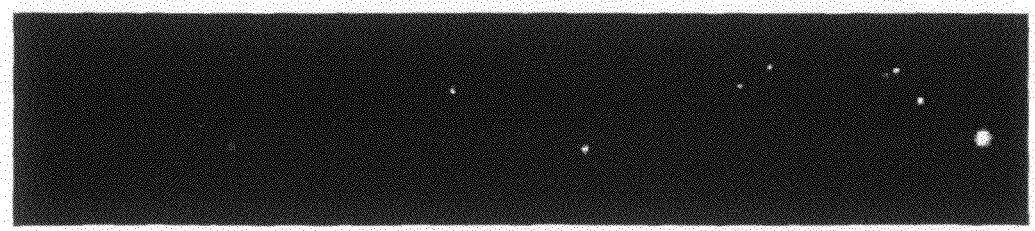
C- Fluorescent-labeled DNA three-dimensionally patterned by direct sorption into polymer

IMMOBILISATION OF BIOLOGICAL MOLECULES

CROSS-REFERENCE TO RELATED APPLICATIONS

This application is the U.S. National Phase under 35 U.S.C. §371 of International Application No. PCT/GB2006/002510, filed Jul. 6, 2006, which claims priority to British Application No. 0513910.0, filed Jul. 7, 2005.

The present invention relates to methods of immobilising biological molecules on to a supporting substrate surface. The invention extends to surfaces having biological molecules immobilised thereon made by such methods, and also to uses thereof. The invention relates to devices where it is necessary to functionalise a surface of a device with a biological entity, for example, medical devices, and implants. Particularly, although not exclusively, the invention relates to methods of manufacturing biosensors, which may be used to detect the presence of chemical or biological analyte molecules, and to biosensors made by such methods.

The increasing effort to produce miniaturized analytical systems has lead to silicon micro-fabrication technology being considered in the manufacturing of biosensors. Biosensors may consist of a silicon support substrate, to which is attached either a specific species of biological molecule, or a variety of different species of biological molecules, depending on the nature of the target analyte(s) being investigated by the sensor. For example, the biological molecule attached to the support substrate of the biosensor may be a specific sequence of DNA molecule, protein, antibody, enzyme, or a whole cell etc. Alternatively, biosensors exist which have a variety of different species of DNA molecules, proteins, antibodies, enzymes, or cells attached to the support surface.

By way of example, if the biological molecule to be investigated (i.e. the analyte molecule) by the biosensor is a particular antigen, the substrate of the biosensor may have antibodies attached to it, which antibodies each have the same specific structure as each other, and each of which exhibit immunospecificity for that particular target antigen analyte molecule. The antibodies are attached to the support substrate in a very site-specific arrangement in order for the biosensor to function effectively. The biosensor coated with the antibodies is then exposed to a solution containing the target antigen analyte, whereupon the antigen will bind to the antibodies on the biosensor. This binding event may be detected in a number of ways. In the case of a piezoelectric biosensor, the change in the mass caused by the binding of analyte to the specific region of the biosensor causes a variation in the resonant frequency of that region of the biosensor. This change in resonant frequency may then be used to calculate the value of the applied mass to the sensor, and hence, the mass of the analyte antigen. Such biosensors are known in the art as resonant mass sensors, an example of which is described in patent application, PCT/GB02/00237.

It will be appreciated that a major limitation in the development of any biologically integrated device, such as a biosensor, is the ability to immobilize biomolecules, such as antibodies, DNA sequences, cells, or enzymes etc, in a highly accurate, site-specific way onto a defined target surface such that the biological species is immobilised at high density and with a high degree of biological activity being retained. Due to the very small scale of biosensors, maximising the amount and activity of biological molecules immobilised in this way is essential for ensuring the sensitivity of such devices. Furthermore, it is an important requirement to be able to immobilise or "pattern" the biomolecule(s) onto the target surface with a very high accuracy. In addition, the ability to pattern several different types of biological molecule on to selected regions of the support surface is a major issue for the development of multi-analyte detection devices. The ability to develop methodologies with such characteristics, which are robust, reproducible and also compatible with clean room and manufacturing processes remains a challenge in the prior art.

One technique currently used for immobilising biomolecules to a support surface is known as the "soft lithography technique" based on micro-contact printing of the biological molecules onto a solid substrate. Soft lithography involves initially manufacturing an elastomeric stamp using Polydimethylsiloxane (PDMS), which is inked into a biomolecule solution in order to transfer the feature of interest to a solid substrate surface through conformational contact. With this simple procedure, a monolayer of protein can be directly patterned onto the required surface or selectively reacted with a patterned monolayer of anchor-molecules, such as functionalized thiols onto gold, or functionalized silanes onto silicon oxide. A problem with these methods is that the inked stamp has to be accurately aligned to the surface, involving a serious complication in the manufacturing process. Moreover, the amount of biological molecules immobilized cannot exceed one monolayer, representing a significant potential handicap for miniaturized biorecognition devices to reach a high sensitivity.

An alternative method has been proposed by Salloum et al. (Biomacromolecules 2004, 5, 1089-1096) where they created a "polyelectrolyte multilayer" (PEMU) thin film based on electrostatic interactions, which has the ability to be loaded with proteins. The major aim of this work consisted in proving that the amount of biomolecules immobilised into the three-dimensional PEMU increases with its thickness. However, a major limitation of such three-dimensional structures built through electrostatic interactions, is their high sensitivity to the nature of the solvent used, as well as salt concentration, pH and polarity. This lack of robustness make these molecular architectures based on electrostatic interactions incompatible with manufacturing processes.

In parallel to soft lithography techniques, several strategies based on resist lithography are also currently used for patterning biomolecules to a solid substrate. These so-called "lift-off" lithographic techniques involve applying a radiation sensitive material, referred to as a resist, to the substrate surface to which the biomolecule is to be immobilised. The resist is then subjected to radiation at a pre-defined wavelength such that the specific regions of the resist is then be removed from the substrate to uncover the target region of the substrate underneath. The radiation is targeted at pre-defined regions of the resist either using a patterned 'mask' or by using maskless lithography, for example, via an electron-beam (e-beam) exposure. This is known in the art as resist lithography' or 'patterning'. For high-resolution patterning, the resist is exposed to radiation of a high frequency, for example, UV radiation, X-ray radiation, or an e-beam. Once the target areas of the resist have been removed, the biomolecule may then be immobilized on to the exposed part of the substrate.

However, a problem with the current methods in the prior art that use such an approach is that the amount of biomolecule covalently attached to the surface rarely exceeds one monolayer. Furthermore, protein patterning procedures based on conventional "lift-off" lithography techniques described above, which use resist materials, face a serious problem when more than one type of biomolecule has to be patterned on to the same surface. This problem resides in the fact that the organic solvents used to develop and remove the resist material are totally incompatible with most biological materials. Hence, the integration of methods of immobilising biological molecules into lithographic processes remains a key challenge. Therefore, in conventional resist-based lithography, a significant limitation is found when more than one type of biological molecule pattern is required on the same surface, due to the fact that biological molecule immobilization and resist patterning procedures have to cohabitate, despite their incompatibility.

Sorribas et. al. (Biomaterials 2002, 23, 893-900) attempted to address the problem of patterning more than one biomolecule on to a support by embedding a biological molecule monolayer into a sucrose layer, in order to protect a first biomolecule from the photoresist washing step. Using their procedure, they managed to achieve patterning of two biological molecule species on to a support surface. However, in their experiments, they use only one photolithographic sequence, the feature drawn by the second biomolecule occupied all the free space left after the patterning of the first biomolecule. As a consequence, the feature drawn by the first biomolecule was the negative of the second biomolecule, which dramatically limits the versatility of their process.

A further limitation of known immobilisation techniques, is that for many applications they do not allow sufficient quantity or quality of biomolecules to be immobilised on to the surface. For biosensors, this can mean sub-optimal sensitivity, and reduced accuracy when detecting or measuring a target analyte(s). This limitation is resultant on the fact it is considered highly desirable to use methods of immobilisation which favour the formation of highly ordered monolayers of biological molecules which are covalently attached onto the substrate surface. This is thought to be necessary in order to achieve a reproducible, and robust attachment to the surface. However, using such methods of monolayer procedures, it is not always possible to immobilise sufficiently high concentrations of the biological molecule in a biologically active condition on to the support substrate. Not only is there a limited area on the support substrate to which the biological molecules can be immobilised, but the very act of attaching the biological molecules to the substrate by means of covalent bonds or direct adsorption often results in a reduction or even total loss of their inherent activity.

For example, the use of aminopropyltriethoxysilane (APTES) for functionalizing silicon oxide substrates for the attachment of biological molecules has been previously discussed in the literature. The functionalisation reaction is carried out by exposing the substrate to APTES in the presence of a solvent, for example, acetone, ethanol, or methanol, in order to form a single thin monolayer of silane, which forms in a two-dimensional plane along the substrate surface. The silane monolayer is covalently bonded to the substrate and acts as a 'cross-linker' to which a biological molecule may then be covalently attached. However, despite offering a robust and defined method of attachment to the surface, a marked problem with attaching the biological molecule to the silane cross-linker monolayer by covalent bonds, is that a substantial decrease in the amount of the biological molecule's activity tends to occur. This is because a certain proportion of the biological molecules lose their native structure as the covalent bonds formed with the silane cross-linker during attachment. Moreover, the organic solvents, which are commonly used as an APTES solvent are incompatible with resist-based lithographic techniques because they would dissolve the resist within a few seconds.

Therefore, it is an aim of embodiments of the present invention to address the problems with the prior art, and to provide improved methods for immobilising biological molecules on to a support substrate, such that the biological molecules are attached in a robust and reproducible manner to the substrate and that they are immobilised at high concentration while retaining activity. It is a further aim that, if required to position the biomolecules in a precise manner, the method is compatible with high resolution methods of patterning such as lithography. Furthermore, it is a further aim to provide uses of such methods for the manufacture of devices, which require functionalisation with biomacromolecules, such as medical devices, and improved sensors for biological or chemical species.

The inventors wanted to see if it was possible to improve the site-selectivity of immobilising active biological molecules on to a support substrate. They based their investigations on the use of aminopropyltriethoxysilane (APTES), which up until now has only been used to produce a very thin two-dimensional (horizontal) silane monolayer across the plane of the substrate. The silane monolayer acts as a cross-linker for the covalent attachment of biological molecules to the upper surface thereof.

According to a first aspect of the present invention, there is provided a method of immobilising a biological molecule on a substrate, the method comprising:—
  (i) covalently attaching a substantially three-dimensional polysilane polymer to a substrate; and
  (ii) attaching a biological molecule onto and/or within the polymer.

Hence, by the term "three-dimensional polysilane polymer", we mean a cross-linked polymer structure comprising a plurality of silane monomers, which extends substantially along a plane or surface of the substrate (2D) by covalent attachment, and in addition, also extends substantially away from the plane of the substrate (3D), whereby saline molecules are covalently attached to other silane molecules, which are either directly or indirectly attached to the substrate.

By the term "substrate", we mean any suitable surface to which the polysilane polymer, and hence, biological molecule may be attached.

By the term "biological molecule", we mean any organic molecule with a biological activity and/or specificity, for example, a macromolecule from a living organism. For example, the biological molecule may comprise a nucleic acid molecule, which may be single-stranded or double-stranded (e.g. DNA, RNA or any such chemical substitutes such as PNA etc), amino acid, antibody, peptide, protein, enzyme. The biological molecule may comprise a whole cell, or part of a cell, a virus, phage, or a micro-organism, or an organelle, or a virus particle etc. For convenience, the terms "biological molecule", "biomolecule", "biological element", and "bioelement", used all herein are used interchangeably.

Current technology, which immobilises biological molecules on to substrate surfaces includes using aminopropyltriethoxysilane (APTES) to form a two-dimensional silane monolayer across the surface of the substrate, i.e. the monolayer extends only parallel with the plane of the substrate. This is achieved by using organic solvents, such as toluene, acetone, methanol, ethanol or water, during the APTES silanisation reaction. These currently used methods involve the use of non-alkaline conditions. The 2D silane monolayer acts as a covalent cross-linker with the substrate to which biological molecules may be covalently attached, or directly adsorbed via electrostatic interactions. This is thought necessary in order to achieve a highly defined and reproducible capture of the target biomolecule.

The inventors decided to go against the teaching of the prior art by attempting to see if it was possible to produce a three-dimensional polysilane polymer, which is covalently bound to the substrate, thereby providing a robust method of attachment to the surface and which also has a highly defined structure, which can be made in a highly reproducible manner. If this were possible then it may be feasible to immobilise biomolecules in a non-covalent manner within and onto the polymer structure. In one embodiment, the inventors investigated the immobilisation of a single type or single species of biological molecule to a substrate. This is referred to herein as the "mono-protein" method, and is described in Example 1. In an alternative embodiment, the inventors investigated the immobilisation of two or more different types or species of biological molecule to a support substrate types. This is referred to as the "multi-protein" method, and is described in Example 2. It will be appreciated that the mono-protein and multi-protein methods are not limited to proteins per se, and extend to the immobilisation of any biological molecule as defined herein, such as nucleic acids, enzymes, cells etc.

The ability of APTES to polymerise to form a three-dimensional and form a polymer network due to its bi-functional character, under the correct conditions, has always been presented in the literature as being undesirable for such applications. This is because the polymerisation reaction of aminosilane monomers has been notoriously very difficult to control, thereby preventing a well-defined and reproducible surface for the effective covalent attachment of the biomolecule. For example, the polymer may not be sufficiently linked to the substrate, and because it would be considered difficult to effectively retain a biological molecule into a polymeric network without losing most of the immobilised material in a reverse desorption process. It will be appreciated that retaining biological activity of the immobilised biological molecule is of particular importance. Accordingly, the methods taught by the prior art have been specifically designed to prevent extensive APTES polymerisation from occurring, by using non-alkaline solvents, principally toluene.

To their surprise, the inventors found that it was possible to produce a three-dimensional polysilane polymer network, which was highly regular in structure and covalently attached to the substrate. Furthermore, what was even more surprising was that the inventors found that they were able to immobilise in a very site-specific manner, very high concentrations of a biological molecule into the polysilane polymer network. This was totally unexpected for several reasons. Firstly, the inventors did not expect a polysilane polymer to effectively absorb biological molecules in such high concentrations. This was because they did not expect that the polymer network would be porous and therefore suitable for absorbing biomolecules therein. Secondly, due to the complexity of the interactions of biomolecules exposed to a chemical environment, it was totally unpredictable that the biomolecules would be bound to the polymer in such an active state, even if electrostatic interactions and hydrogen bonding are known to be sufficiently non-degrading in respect most of biomolecules' active structure. As mentioned above, this is particularly advantageous.

Therefore, the method according to the invention solves the problems with the prior art, and describes a simple, robust and novel procedure, which enables the three-dimensional immobilisation of biological molecules on to a support substrate with a very high degree of accuracy, or resolution. The method according to the invention may comprise creating a polysilane polymer across substantially the entire surface of the substrate. However, preferably, the method comprises creating a polysilane polymer in selected 'target' regions of the substrate surface. This may be achieved by using "lift-off" resist-based lithography.

"Lift-off" resist-based lithography is known to the skilled technician, and the steps used are shown in FIG. 1. The substrate may be first coated with a radiation sensitive material, referred to in the art as a 'resist'. The radiation sensitive material may be targeted with a threshold level of radiation at a pre-defined wavelength, upon which the radiation sensitive material will then be removed from the substrate to uncover the target region of the substrate. This is known in the art as 'resist lithography' or 'patterning'. For high-resolution resist patterning, the radiation sensitive material is exposed to radiation of a high frequency, for example, UV radiation, X-ray radiation or e-beam. The threshold level of radiation required to remove the radiation sensitive material from the substrate depends on the type of material that is being used.

Examples of suitable radiation sensitive material, which may be used in the method of the invention include polymethylmetacrylate based resists (PMMA), water soluble poly (methyl acrylimidoglycolate methyl ether) (poly(MAGME)), or poly(mono-isobornyl 2-(4-vinylbenzyl)malonate) based resist. However, a preferred radiation sensitive material includes a Novolac™ based photoresist layer, which is sensitive at high resolution to UV.

Methods for coating the substrate with a suitable radiation sensitive material will be known to the skilled technician. For example, the material may be coated on the substrate by spraying a commercial resist, preferably, uniformly all over the surface.

However, the material may be spin-coated on to the substrate, for example, using the methodology described in the Examples. Following spin coating, the radiation sensitive material covering the substrate may then be cured. Curing may be carried out by heating the substrate at a suitable temperature for a sufficient time, for example, in excess of 95° C. for several minutes, or at room temperature for a few days.

The regions of the substrate on to which the biological molecule will be ultimately immobilised (i.e. the target region), is then preferably transferred to the radiation sensitive material covering the substrate, preferably by exposure to radiation. This may be achieved using standard lithography techniques, for example, by using either a lithographic mask or by using maskless lithography techniques, both of which will be known to the skilled technician. For example, the radiation sensitive material covering the substrate may be exposed to a wavelength of radiation to which it is sensitive (for example, UV), which causes the material to be removed at positions, which correspond to the target site. This results in the target region on the substrate being exposed, but leaves non-target site regions of radiation sensitive material in position on the substrate. The exposed target site of the substrate is then preferably subjected to an "in situ" polymerisation reaction. This represents a preferred step (i) of the method of the first aspect of the invention.

By the term "in situ polymerisation reaction", we mean that a polymer is directly formed at the positions of the exposed target site on the substrate.

It is preferred that the chemical reaction which takes place during the polymerisation reaction according to the method of the invention is a nucleophilic substitution. Nucleophilic substitution will be known to the skilled technician and involves a nucleophilic group (N), an electrophile group (E) and a leaving group (L), as illustrated in FIG. 18. The nucleophilic group (N) is rich in electrons and attacks the electrophilic group (E), which is deficient in electrons, resulting in a covalent bond between them.

This polymerisation reaction according to the invention may comprise the polymerisation of an organosilane monomer, which is preferably bifunctional. By the term "bifunctional", we mean that the structure of the molecule allows it to react with another identical molecule creating a network of covalently cross-linked polymer.

Preferred organosilane monomers may contain on the same molecule, at least one nucleophilic group. Suitable nucleophilic groups may include amines, thiols, thiocyanates, cyanate or alcoholate.

Preferred monomers may contain at least one leaving group, preferably, attached to the silicon atom. Suitable leaving groups may include alkoxy, halogen or silazane. Suitable halogens include fluoride, chloride, bromide, or iodide.

The organosilane monomer may have the following formula:—

Formula I

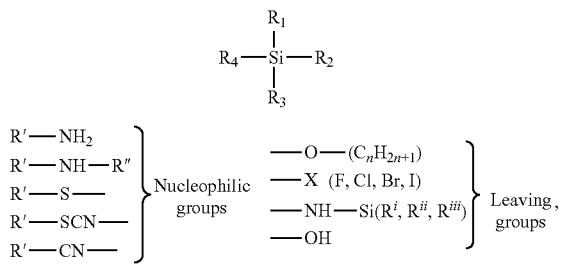

wherein at least one of $R_1$, $R_2$, $R_3$, and $R_4$ comprises at least one leaving group, and at least one of $R_1$, $R_2$, $R_3$, and $R_4$ is a nucleophilic group. Preferably two or three of $R_1$, $R_2$, $R_3$ and $R_4$ are leaving groups. Examples of suitable leaving groups include alkoxy, halogen, silazane or hydroxyl. Examples of suitable nucleophilic groups include amine, thiol, thiocyanate, cyanate, or alcoholate.

The spacer R' in the nucleophilic group may be saturated or unsaturated. The spacer R' may be aliphatic or aromatic. The length of the spacer R' may be between C1-C10. The substituent R" in the secondary amine formula referred to in the nucleophilic group may be saturated or unsaturated. The R" may be aliphatic or aromatic. The length of R" may be between C1-C10. In the semi-developed formula of the leaving groups illustrated in Formula I, the substituents $R^i$, $R^{ii}$ and $R^{iii}$ may be for instance alkyl, alkoxy hydroxyl, halogen, but the list is not exhaustive.

Preferably, the polymerisation reaction comprises the polymerisation of alkoxysilane and/or aminosilane monomers. Suitable alkoxysilane monomers may comprise C1-C10 silane, or C1-C10 oxysilane. For example, the monomer may comprise methoxysilane, ethoxysilane, or propoxysilane.

However, in a most preferred embodiment, the polymerisation reaction may comprise the polymerisation of 3-aminopropyltriethoxysilane (APTES), i.e. $(CH_3CH_2O)_3Si(CH_2)_3NH_2$. The formula of APTES is shown as Formula II:—

Formula II

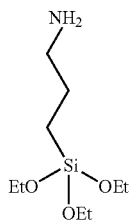

A schematic diagram of the APTES polymerisation reaction is shown in FIG. 3. The nucleophilic group is the primary amine and the electrophilic group is the silicon atom. The number of covalent bonds that an atom can share with other atoms is dictated by its valence, and in the case of silicon, the valence is 4. This means that when the primary amine (ie. the nucleophilic group) shares a covalent bond with the silicon atom (i.e. the electrophilic centre group), then this atom has to break an existing covalent bond which links it to another group, called the leaving group. At the end of the reaction, the leaving group, which was covalently attached to the electrophilic group, has been substituted by the nucleophilic group. In the APTES polymerization reaction, at least one ethoxy group of an APTES molecule is preferably substituted by at least one primary amine of another APTES molecule.

The concentration of APTES used in the method may be between 0.1%-20% (v/v). However, preferred concentrations of APTES are between 0.2-10% (v/v), more preferably, between 0.5-5% (v/v), and most preferably, between 1-3% (v/v).

Preferably, the polymerisation reaction is carried out in substantially alkaline (or basic) conditions. For example, it is preferred that the polymerisation reaction is carried out in an alkaline solvent, which may be organic. It is preferred that the solvent is strongly basic, and may have a pKa which is higher than 8. Preferably, the pKa is higher than 9, 10, or 11, and most preferably higher than 12.

Preferably, the solvent does not contain hydroxyl groups. This is because hydroxyl groups are nucleophilic and would otherwise interfere with the polymerisation reaction Suitable solvents may include benzylamine, n-butylamine, diethylamine, dimethylamine, ethylamine, ethylenediamine, methylamine, triethylamine or trimethylamine. In a most preferred embodiment, the solvent comprises triethylamine (TEA). The pKa of TEA used as solvent in the polymerisation reaction is preferably, above 11. Preferably, a solution of TEA ($\geq$about 98%) is used for the polymerisation reaction.

For most effective "in situ" polymerisation to take place, the resist-patterned substrate is preferably left in the presence of the organosilane monomer and base, for at least 1 hour, more preferably at least 2 hours, and even more preferably, at least 5 hours. The polymerisation reaction may be carried at a temperature in between 15° C. to 80° C. However, preferably, the polymerisation reaction takes place at room temperature (21° C.). It is most preferred that the polymerisation reaction comprises use of approx. 2% (v/v) APTES (aminopropyltriethoxysilane) in substantially pure triethylamine, preferably at about 21° C.

Preferably, if radiation sensitive material has been used, any radiation sensitive material or any non-covalently attached molecules, remaining on the substrate may then be removed by procedures, which will be known to the skilled technician. For example, the substrate may be dried, preferably, under an air stream. The substrate may then be sonicated in a suitable solvent, for example, acetone for sufficient time to remove the material. About 5 minutes is sufficient, and this results in removal of substantially the rest of the radiation sensitive material from the substrate. However, it should be appreciated that at this stage, the polymerisation reaction is not totally complete. Accordingly, preferably, the substrate may then be cured. The curing step may be achieved by heating the substrate for sufficient time at a suitable temperature. For example, the substrate may be heated to about 120° C. or over, for at least approximately 1 to 3 hours.

During the curing step, any residual organosilanes may be removed from the substrate by evaporation. A high temperature during the curing step enables the chemical system to reach the energy of activation required for the polymerisation reaction to take place, leading preferably to the formation of the polysilane polymer on the substrate. An illustration of the polymerisation reaction is shown in FIG. 3. Preferably, the polymerisation reaction comprises the formation of covalent bonds between the substrate surface and silane monomers. Accordingly, the result of the polymerisation reaction is the production of a cross-linked polysilane polymer network, which is covalently bonded to the substrate surface as in step (i) according to the method of the first aspect. In addition, preferably, the polymerisation reaction comprises the formation of siloxane bonds between adjacent silane monomers, which form by siloxane lateral condensation extending away from the plane of the substrate.

Therefore, a preferred step (i) of the method of according to the invention comprises attaching the polysilane polymer to the substrate in a substantially three-dimensional orientation, i.e. substantially parallel to the plane of the substrate (in two dimensions), and in addition, also substantially transverse to, or away from, the plane of the substrate (in three dimensions).

The inventors were surprised to find that by slightly adjusting the various parameters of the polymerisation reaction of step (i) of the method, it was possible to vary the thickness of the polysilane polymer attached to the substrate, while still retaining its uniform structure (and hence, ability to retain biomolecules), and its ability to be precisely positioned on the surface. By varying the time for the polymerization reaction from between a few minutes to 12 hours, and in addition, by varying the time for the sonication step in acetone, the polymer thickness may form from a few nanometers to a few micrometres. The skilled technician will know how to measure the thickness of the polysilane polymer, for example, by using surface profilometric techniques or Atomic Force Microscopy (AFM).

Suitably, the polymer is at least 10 nm in thickness, more suitably, at least 25 nm thick, even more suitably at least 50 nm thick, and most suitably, at least 100 nm thick. The inventors found that a polymer of such thickness had utility for the subsequent attachment of biomolecules thereto in step (ii) of the method according to the invention. However, they found that it was possible to further increase the concentration of biomolecules attached to the polymer, by increasing the thickness of the polysilane polymer even more. Hence, preferably, the polymer is at least 150 nm thick, more preferably at least 200 nm thick, and even more preferably, at least 500 nm thick.

It will therefore be appreciated that the inventors have devised a surprisingly effective technique for attaching high concentrations of biomolecules to a substrate by attachment to the polysilane polymer. While the inventors do not wish to be bound by any hypothesis, they believe that in complete contrast to the teaching of the prior art, which teaches to ensure that the polysilane layer formed on the substrate is a two-dimensional monolayer, whereas in the method according to the first aspect of the invention, the thicker the polysilane polymer formed on the substrate, the better. This is because an improved attachment of the biological molecule thereto may be achieved.

Therefore, if the maximum amount of immobilised biomolecule is needed to be attached to the polymer, it is most preferred that the polymer on the substrate is at least 750 nm in thickness, more preferably, at least 1000 nm thick, even more suitably at least 1500 nm thick, and most suitably, at least 2000 nm thick. In fact, the inventors believe that forming a polymer, which is several micrometres (3 μm to 10 μm) in thickness, would be most advantageous for the subsequent attachment of biomolecules thereto.

Following the production of the polysilane polymer on the substrate, a biological molecule was then contacted therewith in accordance with step (ii) of the method of the invention. Following preparation of the polymer attached to the substrate by step (i) of the method, step (ii) comprises contacting the polymer with the biological molecule. For example, a preferred step (ii) of the method may comprise incubating the substrate in a suitable buffer solution containing a suitable concentration of the biological molecule to be attached. Examples of suitable buffer solution may include acetate buffer, HEPES (N-2-hydroxyethylpiperazine-N'-2-ethanesulfonic acid), IVIES (2-(N-morpholino ethanesulfonic acid), MOPS (3-(N-morpholine) propanesulfonic acid), TRIS (tris(hydroxylmethyl)aminoethane), PIPES (piperazine-N—N'-bis(2-ethanesulphonic acid), or carbonate buffer.

However, a preferred buffer comprises Phosphate Buffer Saline (PBS buffer). A suitable concentration of the biological molecule in the buffer will depend on the type and concentration of biological molecule to be attached, and will be known to the skilled technician. However, by way of example, a suitable concentration of a typical enzyme, will be between about 10 and about 100 μg mL$^{-1}$.

The substrate may be contacted with the biological molecule for sufficient time and at a suitable temperature to allow the biological molecule to become attached to the polysilane polymer. Preferably, the biomolecule is absorbed and/or adsorbed onto and into the polysilane polymer in step (ii) of the method according to the invention. Preferably, the biomolecule is absorbed and adsorbed onto and within the polymer. Again, incubation times and temperatures will depend greatly on the type of biological molecule being attached. By way of example, suitable incubation times may be between about 10 minutes to about 5 hours. Most preferred incubation times may be for about 1 hour. The temperature of the incubation may be between about 21° C. to about 37° C. Following contacting with the biological molecule, the substrate may then be rinsed, for example, in further buffer solution (not containing any biological molecule) and/or water. The substrate may then be stored in a fridge (4° C.) before use.

The biological molecule may comprise a nucleic acid molecule, which may be single-stranded or double-stranded (e.g. DNA, RNA etc), an amino acid, peptide, protein, enzyme, antibody, or a cell etc. The inventors investigated the efficacy of immobilising several different types or species of biological molecule on to the substrate surface in order to test how well the methodology worked. Examples of such biological elements under examination included enzymes, antibodies, and nucleic acid (DNA) molecules.

Hence, the biological molecule to be attached in step (ii) may be an enzyme, in which case the substrate comprising a polymer may be left in a buffer solution containing an enzyme. As an example of an enzyme, the inventors used Horseradish peroxidase (HRP), which was labelled with the fluorescent dye fluorescein isothiocyanate (FITC). Following preparation of the polymer attached to the substrate by step (i) of the method, step (ii) comprises incubating the substrate in a suitable buffer solution containing a suitable concentration of the biomolecule. A preferred buffer comprises PBS solution. A suitable concentration of the biomolecule in the buffer will depend on the type of biomolecule, and will be known to the skilled technician. However, by way of example, a suitable concentration of a typical enzyme, such as Horseradish peroxidase will be about 100 μg mL$^{-1}$.

The substrate may be incubated in the buffer containing the enzyme for sufficient time and at a suitable temperature to allow the enzyme to become attached to the polymer. By way of example, a suitable incubation time may be about 1 hour. The temperature of the incubation may be at room temperature (about 21° C.). Following incubation in the buffer solution containing the enzyme, the substrate may then be rinsed, for example, in further buffer solution (not containing any biological molecule) and/or water.

The biological molecule to be attached in step (ii) may be an antibody, in which case the substrate comprising the polysilane a may be left in a buffer solution containing an antibody. A suitable concentration of antibody may be about 10 µg mL$^{-1}$. The substrate may be incubated for about 1 hour at an incubation temperature of about 37° C. The excess of antibody may then be removed by shaking gently the samples with washing buffer or water, for about 5 minutes. An example of a washing buffer includes 0.05% Triton X100 in PBS. The substrate surfaces are then preferably treated with an antibody blocking solution. An example of a suitable blocking solution is 0.5% BSA in PBS. The blocking treatment may be for about 1 hour at 37° C., followed by further rinsing, and optionally, further washing.

The biological molecule to be attached in step (ii) may be a nucleic acid, in which case the substrate comprising the polymeric may be left in a buffer solution containing a nucleic acid. By the way of example, a DNA sequence, which may be labelled with Rhodamine red dye, may be directly absorbed/adsorbed from a DNA buffer solution into the polymer. A suitable DNA concentration may be around 0.3 µM.

The inventors have found that the step of attaching the biological molecule to the polysilane polymer (step (ii) of the method) may comprise either absorption (i.e. the biological molecule penetrates in to the polymer and is contained therein by means of relatively weak electrostatic interactions between the biological molecule and the polymer itself) and/or adsorption (i.e. the biological molecule is weakly attracted to the surface of the polymer). The inventors were very surprised to see that the polysilane polymer had the ability to absorb biological molecules into, and also onto, its cross-linked three-dimensional porous structure.

While they do not wish to be bound by any hypothesis, the inventors believe that the biological molecules are absorbed into the gaps or spaces formed between the cross-linked silane monomers of the polymer, as illustrated in FIG. 3. They believe that because the biological molecules are maintained within the polymer structure by means of weak electrostatic interactions (and not covalent bonds), the molecule retains its biological activity to a surprisingly effective degree. Furthermore, the resolution of attaching the biological molecule to the polymer and hence, the substrate was very high using the method according to the invention, i.e. to approximately 1 µM resolution, and could probably be improved to a few hundred of nanometres if combined with high definition e-beam lithography. Because the polymerisation process takes place "in situ", the authors believe that the resolution of the polymer pattern is only limited by the size of the features, which are created during the lithographic step onto the resist. In the case of lithographic e-beam, the resist is exposed to an electron beam, which draws the required feature on the surface of the resist, improving dramatically the resolution to a nanometric scale comparatively to the UV based photolithographic techniques.

It will be appreciated that the method of the invention may be used to immobilise biological molecules on to virtually any substrate surface. For example, the method of the first aspect may be used to immobilise biological molecules on any one surface, where it is necessary to functionalise with a biological entity, for example, surfaces of medical devices, and implants. Therefore, for example, the substrate may comprise any solid surface, such as glass, metal, such as, gold, silver, platinum, palladium, etc. However, the inventors were particularly interested in developing biosensors, which may be used to investigate target analyte molecules, which may comprise a silicon oxide base surface. Hence, it is most preferred that the substrate comprises silicon oxide. Accordingly, the method of the invention may be used in the manufacture of any system where it is desirable to functionalize the surface with high concentration of active macro-biological species, including miniaturised analytical systems such as biosensors, or implantable medical devices.

When the substrate comprises a metal such as gold, the method may comprise a step for pre-functionalising the substrate, prior to the step (i) of attaching the polysilane polymer thereto. In embodiments of the method in which radiation sensitive material may be coated on the substrate, the pre-functionalising step may be carried out either before or after the radiation sensitive material is applied. For example, a layer of amine groups may be contained within a sulphur-containing molecule, for example, cystamine or cysteamine. Such aminodisulphides or aminothiols are known to chemisorb onto gold and form very compact and organised monolayers. This may be used to react with organosilanes as a starting point for the polymerisation reaction.

In summary, the inventors have investigated the immobilisation (i.e. attachment) of one type of biological molecule on to a substrate using highly accurate lithography patterning techniques. The attachment of the biological molecule to the substrate is achieved in a three-dimensional orientation, i.e. parallel to the plane of the support substrate, and also substantially transverse to the plane of the substrate. The polysilane polymer is first formed on the substrate in step (i) of the method. After removing radiation sensitive resist material (if used) with acetone, the biological molecule is then physically adsorbed and/or absorbed into and onto the sponge-like three-dimensional polysilane polymer structure in step (ii) of the method. In contrast to prior art patterning techniques, where the substrate background and the chemical pattern formed by lithography share the same planar dimension, the amount of biological molecule selectively patterned using the method of the first aspect of the invention is, surprisingly, up to several orders of magnitude superior to the biomolecule contained in the monolayer not specifically adsorbed onto the pattern-free regions.

The "in situ" polymerisation reaction is based on the bi-functionality of organosilanes, which react, under strongly basic conditions, first with the silicon oxide surface and then with the aminosilane molecules from the solution. The use of an organic base in the method of the invention, such as, triethylamine (TEA) as a solvent makes the chemical process (the polymerisation reaction) efficient and fully compatible with a large number of resists, including the Novolac-based family, which are most commonly used in the manufacture of standard biosensors. Advantageously, the polymerisation reaction takes place under very gentle conditions, at room temperature and under air atmosphere. Once patterned onto the silicon surface, the polymer is very stable in aqueous environment, and shows a high ability to absorb biological molecules on and within its three-dimensional structure.

As described in the Examples, the structure of the polysilane polymer and biological molecules attached thereto has been characterized by Electron Scanning Microscopy (SEM), Atomic Force Microscopy (AFM) and Confocal Microscopy. Several different types of biological elements, such as DNA, proteins, enzymes and antibodies, have been successfully patterned onto silicon surfaces with a one micron resolution. Such a high resolution is very advantageous for discretely positioning the biological molecule on the substrate support. Moreover, the versatility of this biological patterning technique is not restricted to the silicon microfabrication technology since the whole procedure has also been applied to gold surfaces.

In addition, to immobilising just a single type or species of biological molecule to the substrate, in an alternative embodiment, the inventors also investigated whether it was possible to attach more than one type or species of biological molecule on to the substrate using highly accurate patterning, and this is described in Example 2, with reference to FIG. 2. This would be useful in circumstances where more than one type of biological molecule is required on a surface.

Hence, step (ii) of the method according to the first aspect of the invention may comprise attaching a plurality of different species of biological molecule to the polysilane polymer formed on the substrate. The different species may be attached to the substrate in discrete spaced-apart positions, or mixed together.

The inventors believe that attaching a plurality of different species of biological molecules to a substrate will have utility, for example, in the manufacture of multi-analyte biosensors. As the first embodiment as described in Example 1, the attachment of the plurality of biological molecules to the substrate is also achieved in a three-dimensional orientation, i.e. parallel to the plane of the support substrate and also transverse to the plane of the substrate.

As in the first embodiment of the first aspect of the method, step (i) of the second embodiment preferably comprises producing a substantially three-dimensional polysilane polymer on the substrate. The polymer may be attached to the entire surface of the substrate or at pre-defined target sites. Following this step, the polymer is then preferably coated with a chemically protective layer, which layer is adapted to protect the polymer from unwanted subsequent chemical treatment. Examples of suitable chemically protective layers include sucrose, or hydrocolloids like Agar gel, cellulose, gellan gum, pectin or carrageenan which are thermoreversible gels. However, a preferred chemically protective layer comprises gelatin. The chemically protective layer may be coated on to the polysilane polymer by suitable means, for example, by spin coating the substrate in the presence of a solution of gelatin at a suitable concentration (e.g. 50 $\mu g\ mL^{-1}$), as described in Example 2.

It is preferred that the chemically protective layer is about 1 nm-1000 nm in thickness over the polysilane polymer, more preferably, about 10 nm-750 nm thick, even more preferably, about 100 nm-500 nm thick, and most preferably, about 200 nm-400 nm thick. The inventors found that this is the optimum thickness for protecting the polysilane polymer from subsequent unwanted chemical treatment as will be described hereinafter.

The method then preferably comprises a step of coating the substrate (or the chemically protective layer) with a layer of radiation sensitive material, preferably, using standard lithography techniques. Preferred methods are described herein. Once the radiation sensitive material covers the chemically protective layer, the substrate is then preferably exposed to a source of radiation, using standard etching techniques. For example, either masked or maskless lithography may be used to etch or pattern the radiation sensitive material. The development resist step is required to remove the radiation sensitive material from a pre-defined region of the substrate to uncover a first target region of polymer present on the substrate, upon which the biological molecule is intended to be immobilised.

It is preferred that an additional development step is carried out during the resist patterning process, preferably with warm water (about 37° C., for about 1 min). Advantageously, this creates a confined region where the polysilane polymer will then be exposed for the subsequent step in which a biological molecule is attached thereto.

The method then comprises a step of contacting a first species of biological molecule with the substrate. Preferably, the substrate is incubated in the presence of a first species of biological molecule. It will be appreciated that the method is not limited to the particular biological molecule being attached to the polymer. For example, the biological molecule may comprise a nucleic acid molecule (e.g. DNA, RNA etc), amino acid, peptide, protein, enzyme, or cell etc. Preferably, the incubation step is conducted in a suitable buffer at a suitable temperature for sufficient time in order for the biological molecule to become attached to the target region on the polymer.

Following attachment of the biological molecule to the polymer, the method preferably comprises a step of again coating the substrate with a chemically protective layer. Preferably, the chemically protective layer protects the substrate from the following chemical treatments and is preferably, the same as that used in the previous step. Hence, a preferred chemically protective layer is gelatin. This chemically protective layer may be spin coated on to the substrate.

Preferably, the substrate is again exposed to radiation in order to remove selected target regions of the radiation sensitive material. For example, if UV radiation is used previously to remove target regions of the radiation sensitive material, then UV radiation will be used in this step to remove the material. As above, the lithography step may be carried out with or without a mask. Following a subsequent development step, and second target regions of the polymeric is now exposed and free to absorb a second species of biological molecule. Preferably, the second species of biological molecule is different to the first species of biological molecule. For example, it may be a different sequence of nucleic acid molecule (e.g. DNA, RNA etc), amino acid, peptide, protein, enzyme, or cell etc. Alternatively, the second species of biological molecule may be a different type of molecule altogether. For example, the first species of biological molecule may be a nucleic acid, and the second species of biological molecule may be a protein, and so on.

A further coating of chemically resistant material may then be coated over the substrate. Hence, by repeating the steps of patterning and attachment of biological molecules to the polysilane polymer 'n' times, 'n' different biological molecules may be selectively attached onto the polymer on the substrate. The following step of the method consists of removing any remaining radiation sensitive material, and any remaining chemically resistant material. This may be achieved for example by consecutively soaking the samples in acetone and warm water.

The final step of the method comprises blocking the surface of the substrate with a suitable blocking agent, for example, 0.5% of BSA in PBS in order to prevent non-specific protein adsorption/absorption.

Accordingly, in extension to the first embodiment of attaching one species of biological molecule in a three-dimensional manner to the substrate, the second embodiment comprises attaching a plurality of species of biomolecule to the substrate. In conventional resist-based lithography, a significant limitation is found when more than one type of biological molecule pattern is required on the same substrate surface. This is due to the fact that biomolecule immobilization and resist patterning procedures have to cohabitate, despite their incompatibility. The inventors of the present invention have therefore surprisingly found that one way to circumvent this problem consists in insulating or protecting the freshly patterned biomolecule with a thin gelatin layer spin-coated onto it, which acts as a protective layer from any chemical treatment. This procedure makes the manipulation of sensitive biological molecules fully compatible within standard micro-fabrication processes, for example in the manufacture of multi-analyte biosensors. Combination of the three-dimensional biological molecule patterning technique and gelatin protective procedure produces a robust multi-biomolecule patterning procedure, with the number of diverse biological molecules site-selectively immobilized to a substrate surface being theoretically unlimited.

The invention extends to substrates that have been produced using the method according to the first aspect.

Hence, according to a second aspect of the present invention, there is provided a substrate comprising an immobilised biological molecule obtainable by the method according to the first aspect.

The substrate may be used as, or in the manufacture of, any device where it is necessary to functionalise a substrate surface of the device with a biological entity.

Accordingly, in a third aspect there is provided a device comprising a substrate obtainable by the method according to the first aspect.

For example, the device may be a medical device, or an implant, or for instance in bioreactors, or a protein capsule. However, it is preferred that the device is biosensor.

Hence, in a further aspect, there is provided a method of manufacturing a biosensor comprising use of the method according to the first aspect, wherein the substrate is a biosensor.

It will be appreciated that biosensors are analytical devices, which comprise a biologically sensitive element (a biological molecule) and a physical or chemical transducer (substrate), and which are adapted to selectively and quantitatively detect the presence of specific compounds (analytes) in a given environment. Despite the type of biosensor, the biomolecule has to be immobilized in such a way that any change due to the specific biological recognition may be captured by the transducer. Hence, during the manufacture of the biosensor, it may be important to be able to control the location of the biological molecule on the transducer, and to ensure that its activity is maintained during the immobilisation process.

One example of a miniature biosensor is an interdigitated electrode (IDE), which consists of attaching a biological molecule either onto gold electrodes or onto silicon gaps, at a micron scale definition or resolution. Another example of a biosensor involves micro-electromechanical systems (MEMS), which consist of miniature electronic devices having integrated mechanical parts on a micrometer scale. It will be appreciated that the ability to site-selectively immobilise the biological molecule onto specific regions of the biosensor is a major issue in their manufacture.

Hence, it is preferred that the methods according to the invention may be used to carry out biological functionalisation of a substrate in order to produce a biosensor. The biosensor may be a MEMS biosensor. An example of such a biosensor is described in the patent application PCT/GB02/00237, and is incorporated herein by reference. The biosensor may comprise a transducer, which may be a mass resonator, which may be a circular disc resonator. The biosensor may be adapted to detect the presence of a biological target analyte. This may be achieved by measuring a frequency shift produced in the vibration modes of the circular disc resonator. Selected regions of the disc resonator may be modified with capture/recognition species to provide sites for specific binding of the target analyte. For example, suitable capture/recognition species may include the biological molecule, such as an antibody. The spatial distribution of added mass produced by the target analyte (for example, an antigen) may disrupt the axisymmetric mass distribution of the resonator.

It will be appreciated that the modes of an axisymmetric (perfect) disc occurs in pairs, and that each pair shares a common natural frequency. This is a property called modal degeneracy. When additional mass is non-uniformly deposited on the biosensor, (when the target analyte is captured by the capture/recognition species), the modal pairs no longer share this common frequency and the resonant frequencies of the modes 'split' by an amount proportional to the amount of added mass (i.e. the mass of the analyte). The magnitude of the frequency split thus provides a measurement of the analyte in question.

The molecular recognition event requires no labelling of any component of the assay system and therefore advantageously, the biosensor has no requirement for integration with expensive signal interrogation technologies (e.g. fluorimetry). In addition, the circular disc resonator is not affected by problems traditionally suffered by resonant mass sensors (e.g. effects caused by temperature and induced stress) since the two modes are equally affected. Hence, the biosensor manufactured using the method according offers considerable promise for the direct detection, and predictions from mathematical modelling as well as the reproducibility of frequency splits obtained in preliminary device testing demonstrate that surface additions of the order of $0.01$ ng cm$^{-2}$ are measurable with this device. This is in agreement with predictions that mass sensitivities up to two-orders of magnitude better than existing mass sensors based on resonant structures (e.g. the quartz micro-balance) are achievable. Such a sensor exemplifies the need to immobilise high concentrations of biologically active protein with a high degree of accuracy on the sensor surface.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying diagrammatic drawings, in which:—

FIG. 1 shows a schematic representation of a three-dimensional protein patterning process in accordance with an embodiment of the invention;

FIG. 2 shows a schematic representation of the three-dimensional multi-protein patterning process in accordance with an embodiment of the invention;

FIG. 3 shows a synthetic reaction route proposed for APTES polymerisation process onto silicon oxide;

FIG. 4 shows micrographs of a) photoresist patterning where the whole silicon surface is recovered with photoresist except the 60 microns diameter cross feature; b) Polymeric network patterned after "in situ" polymerisation and removing of photoresist. The highly defined polymer patterning is visible (dark region); c) 3 microns diameter dots patterned in polymeric network;

FIG. 5 shows scanning electron microscopy images of polymeric network patterned on silicon oxide. Polymer thickness is around 200 nm. The sample has been gold coated, tilt 85° and accelerating voltage 10 kV. Magnifications: (a) 1,000× and (b) 35,000×;

FIG. 6 shows scanning electron microscopy images obtained with a) Environmental SEM. No gold coating, tilt 30° and accelerating voltage 10 kV. Magnification 1,500×. b)

and c) Conventional SEM. Samples coated with gold, acceleration voltage 10 kV. Magnifications: b) 689× and c) 6,130×;

FIG. 7 shows a surface of polymeric network patterned onto silicon obtained by atomic force microscopy (AFM);

FIG. 8 shows a confocal micrograph of a thick polymeric network created onto a glass slide surface;

FIG. 9 shows fluorescent micrographs of proteins absorbed (a, b, c and d) into the polymeric network patterned onto the silicon surface: a) and c) IgG and then FITC-anti IgG; b) FITC-HRP and d) Rhodamine-red labelled DNA sequence. Crosses diameter: 60 microns; dots diameter: 3 microns;

FIG. 10 shows a) Fluorescent Micrograph of patterned polymeric network modified with: 1) no Human IgG but FITC-anti-Human IgG; 2) Human IgG and then FITC-anti-Rat IgG; 3) Human IgG and then FITC-anti-Human IgG;

FIG. 11 shows fluorescent micrographs of polymeric patterned samples modified with an unlabeled 20-base DNA probe and incubate with either a non-complementary DNA sequence labelled with FITC or a complementary DNA sequence labelled with FITC;

FIG. 12 shows a vertical cross-section of FITC-HRP absorbed into the polymeric network, obtained by confocal microscopy;

FIG. 13 shows micrographs of cross features patterned onto silicon surfaces obtained by treating chemically a silicon surface coated with a photoresist mask with: a) 2% APTES in toluene; b) 2% APTES in toluene containing 10% TEA; c) 2% APTES in TEA. For all the chemical conditions: 5 hours reaction time and room temperature. Crosses diameter: 60 microns;

FIG. 14 shows graphic representation of APTES film thickness formed onto silicon surface depending on the solvent used during the silanization reaction. Experimental conditions: 5 hours and room temperature. All the samples were sonicated in acetone after chemical modification. Thickness of APTES layers was evaluated by using surface profilometry and 1.465 as refractive index value;

FIG. 15 shows fluorescent micrographs obtained after incubation of APTES patterned silicon surfaces into a FITC-HRP solution. As described in FIG. 12, APTES patterning was attempted using several chemical conditions: a) 2% APTES in toluene; b) 2% APTES in toluene containing 10% TEA; c) 2% APTES in TEA. Cross diameter: 60 microns;

FIG. 16 shows a surface profile of a thin gelatin layer spin-coated onto silicon, obtained with a Zygo NewView 5020 equipment;

FIG. 17 shows fluorescent micrographs of patterned polymeric network modified with Human IgG where: a) Patterned IgG was not protected with gelatin layer but not exposed to acetone; b) Patterned IgG was not protected with gelatin layer and exposed to acetone for 5 min; c) Patterned IgG was protected with gelatin layer but not exposed to acetone; d) Patterned IgG was protected with gelatin layer and exposed to acetone for 5 min. In the last step anti-Human labeled with fluorescein (FITC) was used to reveal the presence of active Human IgG; and FIG. 18 represents a schematic of nucleophilic substitution, in which a nucleophilic group (N), an electrophilic group (E) and a leaving group (L) are shown.

FIGS. 19A-C shows the three dimensional patterning of a biological element at a nanometer scale. An e-beam patterned silicon die was manufactured through a standard e-beam "lift-off" procedure. The die included a highly defined sentence with character dimensions of 200 mm lines (FIG. 19A). The die was immersed in a 2% v/v solution of APTEA, dried, sonicated in acetone and cured. The polymeric network was nano-patterned on the substrate surface with a very high definition (FIG. 19B). The die was then allowed to incubate in a FITC-labeled DNA solution and washed, resulting in a highly defined sentence "written" in DNA, with character dimensions of 200 mm lines (FIG. 19C).

EXAMPLES

The inventors investigated the efficacy of the method according to the invention to efficiently attach functional biological molecules (such as proteins, enzymes, antibodies, DNA molecules etc) in a highly accurate and site-specific manner on to a support substrate. The use of the method could then be applied to the manufacture of biosensors and other miniaturised analytical systems, which utilise biological molecules.

Example 1 describes the immobilisation of a single type or species of biological molecule or bioelement (i.e. a certain antibody, enzyme or DNA molecule of a specific defined sequence) to a support substrate. This is referred to as the "mono-protein" method. An overview of the procedure used for 3D mono-protein patterning is described in Example 1 and with reference to FIG. 1. Examples 1a-1c explain each of the steps of the 3D mono-protein patterning process in further detail.

Example 2 describes the immobilisation of two or more different types or species of biological molecule or bioelement (for example, different antibodies, enzymes or DNA molecules having different defined sequences) to a support substrate types. This is referred to as the "multi-protein" method.

Materials and Methods

All experiments were carried out on 1×1 cm$^2$ chips cut from silicon oxide wafer. This material formed the substrate surface on to which the biological molecules were immobilised. Prior to any modification, the silicon surface was cleaned by treatment with boiling piranha solution ($H_2SO_4$/$H_2O_2$, 7:3) for 1 hour, and extensively rinsed with de-ionized (DI) water.

As described herein, for polymeric network patterning, aminopropyltriethoxysilane (APTES) and triethylamine (TEA) were purchased from Sigma-Aldrich and Fluka, respectively.

Several biological elements (biomolecules) were directly patterned on to the silicon oxide substrate, or alternatively, were used, for revealing biological molecule patterning after specific recognition binding. The biological molecules included: Unlabeled human IgG (h-IgG); mouse IgG (m-IgG); anti-human IgG labeled with fluorescin dye FITC (anti-h-IgG-FITC); anti-mouse IgG labeled with phycoerythrin red (anti-m-IgG-R-Phy); horseradish peroxidase conjugated with FITC(HRP-FITC); Herring sperm DNA and bovine serum albumin (BSA). These were all purified and provided by Sigma-Aldrich.

DNA sequences were provided by MWG. The single strand DNA probes contained a spacer of 12 carbons and were made with 20 bases. These DNA probes were either unlabelled or labelled with Rhodamine red dye. The non-complimentary and complimentary DNA strands were made of 20 bases and both labelled with FITC.

Type A gelatin was used in the multi-protein patterning procedure (Example 2) and was from porcine skin (approx. 175 bloom) and purchased from Sigma-Aldrich.

Example 1

Overview of the Three-Dimensional (3D) Mono-Protein Patterning Procedure

The inventors investigated the attachment or immobilisation of one type of biological element or biomolecule (i.e.

mono-protein) on to a silicon oxide support substrate using highly accurate patterning. The attachment of the biomolecule to the substrate is achieved in a three-dimensional orientation, i.e. parallel to the plane of the support substrate and also substantially transverse to the plane of the substrate.

The steps used for the three-dimensional mono-protein patterning is shown in FIG. 1. The silicon oxide substrate surface is first coated with a Novolac based resist layer. The feature of interest (i.e. the specific regions of the substrate on to which the biological molecule is to be attached) is transferred from a lithographic mask (not shown) to the resist by UV exposure and chemical development to produce the feature as shown in FIG. 1(a). These standard lithography steps will be well-known to the skilled technician (Kane, R. S. et al. Biomaterials 1999, 20, 2363-2376; Blawas, A. S. et al. Biomaterials 1998, 19, 595-609; Wilson, D. S. et al. Curr. Op. Chem. Biol. 2002, 6, 81-85).

Secondly, the freshly exposed areas of the silicon substrate surface are then chemically modified with an "in situ" aminosilane polymerisation process as shown in FIG. 1(b). This polymerisation step uses aminopropyltriethoxysilane (APTES) and triethylamine (TEA) and is described in detail in Example 1b.

Thirdly, the remaining photoresist material is then removed from the substrate by sonication in acetone as shown in FIG. 1(c).

Fourthly, once exposed to 120° C. for around 3 hours, the polymerisation process is over and the patterned polymeric polysilane network attached to the silicon substrate is then ready to adsorb and absorb biological molecules into, and also onto, its three-dimensional structure, as shown in FIG. 1(d).

Example 1a

Photolithography

Photolithography was used to apply a radiation-sensitive photoresist material to the substrate surface as shown in FIG. 1(a) in a highly site-specific manner. For both the mono-protein and multi-protein patterning procedures (described in Example 2), a positive Novolac-based photoresist (Microposit SPR 220/7) was spin coated onto the silicon oxide substrate support wafer at (3500 rpm, 120 s, acceleration 1000 rpm/s). It was then soft-baked on a hotplate for 5 min at 95° C., giving rise to a 7 micron thickness photosensitive layer of photoresist material extending across substantially the entire surface of the substrate.

Once the photoresist had been soft-baked on a hotplate during 5 min at 95° C., the substrate wafer was then exposed through a photolithographic mask with a broad band mercury lamp for 18 s which irradiates UV. The design and use of suitable masks will be known to the skilled technician familiar with lithography, and will have been pre-prepared so that, upon exposure to the UV radiation (by the mercury lamp), a pre-designed pattern of UV radiation will pass through the mask onto the photoresist material. It will also be appreciated that maskless lithography using, for example, an array of mirrors may be used to site-specifically expose the photoresist material on the substrate. Following exposure to the radiation, the substrate is then developed using two 60 seconds cycles of TMAH based developer (Microposit MF-26A, 0.26 N). Development was stopped with water, and then the photoresist patterned substrate wafers were dried under an air stream. The result of the photolithography is to produce a highly accurate pattern of photoresist material across the upper surface of the substrate wafer. This may now be referred to as a die, and is shown in FIG. 1(a).

Example 1b

Polymeric Network Patterning

Once the photoresist material had been patterned on the substrate, a polymerisation reaction was then carried out as shown in FIG. 1(b). For the "in situ" polymerisation to take place, the photoresist patterned die was left for at least 5 hours and at room temperature in a 2% (v/v) APTES (aminopropyltriethoxysilane) in pure triethylamine. During the polymerisation reaction, a polysilane polymer network structure forms both on the surface of the photoresist material, and also directly on to the exposed silicon oxide substrate in between the regions covered with photoresist material, as shown in FIG. 1(b).

The die was then dried under an air stream, and then sonicated in acetone for 5 min in order to remove the photoresist material, as shown in FIG. 1(c). At this stage, the polymerisation reaction is not complete and the die must then be cured at 120° C. for at least 3 hours. During the curing process, residual aminosilanes are removed by evaporation, and both the siloxane lateral condensation and the cross-linked polymerisation processes can then take place, as shown in FIG. 1(c).

An illustration of the polymerisation reaction scheme is shown in FIG. 3. Referring to FIG. 3(a), the silicon oxide substrate wafer is shown having a series of hydroxy (—OH) groups extending laterally away therefrom. Referring to FIG. 3(b), there is shown a number of aminopropyltriethoxysilane molecules forming covalent siloxane bonds between each other and the silicon oxide substrate. The result of the polymerisation reaction is the production of a three dimensional, covalently attached aminosiloxane polymer network, attached to the substrate, as shown in FIG. 3(c).

The characterization of the patterned polymeric network shown in FIG. 1(c) was carried out using surface profilometry, scanning electron microscopy (SEM), Confocal Microscopy and Atomic Force Microscopy (AFM). The thickness of the aminosiloxane polymer network was determined by using an optical surface profiler (Zygo NewView 5020), considering a value of 1.465 for the refractive index of the organic polymer (Vandenberg, E. T. et. al. J. Colloids. & Interf. Sc. 1991, 147, 103-118). However, the contribution of this refractive index in the profile image was bypassed by sputtering a thin layer of gold (10-20 nm thickness) onto the whole sample, through an automatic sputter coater technique (Agar Automatic A2890, Agar Ltd). The autofluorescent behaviour of the polymeric network made the characterization of its topography possible by using a Confocal Laser Scanning Microscope (Lerca TCS SP2 UV, Leica Miscrosystems Heidebberg). The structural morphology of the silane polymer network was also elucidated by using a conventional SEM (Gemini electron optics, LEO Elektronen mikroskopie Gmb) where the sample was previously gold coated with a thin gold layer (8 nm thick) in order to make the polymer electrically conductive and a tapping mode AFM (Multimode Scanning Probe Microscope, Nanoscope IV controller).

Example 1c

Absorption and Adsorption of Biological Elements on to the Polysilane Polymer Network Following the production of the silane polymer network, a biological molecule (e.g. a specific species of antibody) was then added to the silicon substrate wafer so that it was absorbed therein, and also, adsorbed thereto. Several biological elements (biomolecules) were directly patterned, or used, for demonstrating the highly specific protein patterning after specific recognition binding. Examples of such biological elements included enzymes, antibodies, and DNA molecules. Specific examples included: unlabeled human IgG (h-IgG); mouse IgG (m-IgG); anti-human IgG labeled with the fluorescent dye, FITC (anti-h-IgG-FITC); anti-mouse IgG labeled with phycoerythrin red (anti-m-IgG-R-Phy); and horseradish peroxidase conjugated with the dye FITC(HRP-FITC).

(i) Enzyme Absorption/Adsorption

As an example of an enzyme, the inventors used Horseradish peroxidase labelled with the fluorescent dye fluorescein isothiocyanate (FITC). In the case of HRP-FITC absorption onto and into the patterned polymeric network, polymer network patterned substrate samples were first prepared using the procedure as detailed previously in Example 1b. The substrates were then incubated with a protein PBS solution (100 µg mL$^{-1}$) for 1 hour, at room temperature. HRP-FITC samples were then rinsed successively with PBS and DI water, before being analysed under fluorescent microscopy. These samples showed to be stable during weeks when kept in the fridge (4° C.) and protected from light to avoid the degradation of fluorescein dye. One sample was maintained for 24 hours in a PBS solution and no significant loss of fluorescence intensity was observed, demonstrating the high stability of the absorbed HRP.

(ii) Antibody Absorption/Adsorption

For immunoassay experiments (i.e. antibodies), the polymeric network patterned substrate samples were left in an "antibody probe" PBS solution (10 µg mL$^{-1}$) for 1 hour and at 37° C. The excess of antibody was removed by shaking gently the samples with washing buffer (0.05% Triton X100 in PBS) for 5 min. The substrate sample surfaces were then treated with a blocking solution (0.5% BSA in PBS) for 1 hour at 37° C. and rinsed again with washing solution for 5 min. Finally, the samples were incubated in an antigen solution (10 µg mL$^{-1}$) for 1 hour at room temperature, under gentle shaking, before a last washing step. For example, if the antibody used was mouse IgG (m-IgG), then the antigen used was anti-mouse IgG labeled with phycoerythrin red (anti-m-IgG-R-Phy). Similarly, if the antibody used was unlabeled human IgG (h-IgG), then the antigen used was anti-human IgG labeled with the fluorescent dye, FITC (anti-h-IgG-FITC). In order to control for the specificity of the patterned antibody, a sample where human-IgG was absorbed, was left to incubate with an anti-mouse IgG. The nature of antibodies immobilisation was an absorption process where weak interactions as electrostatic, hydrogen bonding and Van der Waals forces take place.

(iii) DNA Molecule Adsorption/Absorption

The oligo DNA probe was absorbed from a 0.3 µM solution prepared in carbonate buffer pH 9.6, to a polymer patterned sample. The absorption was left for 30 minutes and at room temperature. For the hybridisation experiments, the DNA modified sample was immersed into a washing buffer (0.05% Triton X100 in PBS) for 5 min, under gentle shaking. Any area of polymer that was not loaded with oligo probe was blocked by immersing the DNA-probe coated sample into a blocking solution (100 µg/mL of herring sperm DNA in PBS) for 1 hour and at room temperature. The hybridisation of complimentary and non-complimentary DNA labelled with FITC was carried out by incubating the blocked probe sample into the corresponding 2 µM DNA solution for 2 hours and at 37° C. The modified samples were washed by gentle shaking for 5 minutes in washing buffer and rinsed with deionised water.

Enzyme, and DNA absorption/adsorption into the polysilane polymeric network patterned onto a silicon oxide sample were followed by using Fluorescent Microscopy (Olympus BX2 Light Microscope System), with the filter corresponding to the excitation/emission wavelengths of the label. For the Confocal Microscope experiment carried out with absorbed anti-h-IgG-FITC (10 µg mL$^{-1}$, 1 hour, 37° C.), no polymer patterning was required and the whole surface of a glass slide was modified with a thick layer of polymeric network (around 2 microns). This technique allowed a useful XZ cross-section imaging of the FITC labelled antibody absorbed into the thick polymer layer.

Example 2

Three-Dimensional Multi-Protein Patterning Procedure

The inventors also investigated attaching more than one type of bioelement or biomolecule (i.e. multi-protein technique) on to a silicon oxide support substrate using highly accurate patterning. As with Example 1, the attachment of the plurality of biological molecules to the substrate is also achieved in a three-dimensional orientation, i.e. parallel to the plane of the support substrate and also transverse to the plane of the substrate. The methodology used for this procedure is shown in FIG. 2.

Referring to FIGS. 2(a) and 2(b), the whole surface of the silicon oxide substrate surface is chemically modified with the polysilane polymeric network using the same experimental conditions as detailed in Example 1a (step 1). The substrate surface is then coated with a thin layer of gelatin (200-400 nm thickness) (step 2). This is obtained by spin-coating a gelatin solution (50 µg mL$^{-1}$/DI water) with a photoresist layer (7 microns thickness), as shown in FIG. 2(b).

Then, as shown in FIG. 2(c) the classical photolithographic process takes place in which the substrate is provided with a photoresist coating (step 3), and then exposed to a source of UV radiation through a mask (although it will be appreciated that maskless lithography is equally effective) (step 4). However, an extra development step is carried out with warm water (37° C., for 1 min), creating confined regions where the polymeric silane network is exposed to the solution interface (step 5). As shown in FIG. 2(d), a biological element (BE1) is then added and adsorbed onto the polymer (step 6). It is then re-covered with a thin spin-coated gelatin layer in order to protect it from the following chemical treatments (step 7).

As shown in FIG. 2(e), the silicon surface is exposed once again to UV with another photolithographic mask (step 8), developed again (step 9), and new regions of the polymeric network are free to absorb another biological element (BE2) (step 10). A further gelatin coating is then added (step 11). By repeating the patterning/protein absorption cycle n times, n different biological elements can be selectively patterned onto the silicon surface. The following step consists of removing consecutively the remaining photoresist (step 12) and gelatin (step 13) by consecutively soaking the samples in acetone and warm water. Finally, the surface background is blocked by using 0.5% of BSA in PBS in order to prevent protein non-specific adsorption/absorption (step 14).

Example 3

Results and Discussion

Example 3.1

Background

The conditions required for a strict APTES monolayer to be horizontally (2D) polymerized onto silicon oxide, is described by Vandenberg et al. *J. Colloids. & Interf. Sc.* 1991, 147, 103-118. This is achieved when a 0.4% APTES solution is left to react with a silicon substrate in dry toluene for 1 hour and at room temperature. In such a reaction, the thickness of APTES layer formed on the substrate is not higher than 0.7 nm after curing the sample at 200° C. for 24 h. However, it was possible to achieve a maximum APTES film thickness of 38 nm when the reaction time is extended to 24 hours and the curing process takes place in air for 24 hours. However, this 38 nm thick APTES layer is no longer stable when exposed to water for 24 hours.

In the same study, the authors compared the thickness of APTES films when toluene is replaced by water or organic solvents, such as trichloroethylene, xylene, acetone, ethanol or chloroform, and the values oscillate between only 0.5 to 1.4 nm, after curing at 200° C. for 24 hours. The standard protocols for APTES silanization onto silicon oxide consist of reacting between 0.4% to 5% of APTES diluted in toluene, acetone, ethanol, ethanol, water or a mixture of them, with a reaction time from 30 s to 24 hours and at room temperature. In all these cases, the APTES thickness does not exceed 9 nm in accordance with the declared intention to covalently attach only a monolayer or a thin film of APTES onto the substrate.

The novel concept in the protein patterning procedure described in FIGS. 1 and 2 of the present invention, is based on the site-selective discrimination of the three-dimensional polysilane polymer network between the patterned silicon oxide substrate surface covered with photoresist material, and the planar background surfaces. Hence, the "in situ" polymerisation of APTES, which takes place in the gaps generated by the photolithography technique, is an important feature of the methods according to the invention.

Example 3.2

Three-Dimensional Patterning of a Polymeric Network

In contrast to the prior art, the inventors of the present invention have used a highly basic (alkaline) organic solvent with no nucleophilic character, such as TEA, which allows APTES to establish siloxane bonds between molecules which form the first monolayer onto the silicon surface (horizontal 2D polymerisation), and then with the molecules from the solution (vertical 3D polymerisation), in order to obtain a siloxane polymer with a thickness from 200 nm to several microns, depending on the experimental conditions used, as illustrated in FIG. 3.

Furthermore, because the chemical process is fully compatible with conventional Novolac based photoresists, any patterning made by this photolithographic technique can be used as a mask for the "in situ" polymerisation process. Referring to FIG. 4, there are shown a series of micrographs of polysilane polymer patterning on the silicon oxide substrate of a biosensor. Referring to FIG. 4(*a*), there is shown the position of four segments of photoresist material on the biosensor. The diameter of the cross-shape of photoresist is 60 µm in diameter. Referring to FIG. 4(*b*), there is shown the dark areas formed by polysilane polymer following in situ polymerisation, and removal of the resist material. Referring to FIG. 4(*c*), there is shown a series of 3 µm diameter dots patterned in the polymeric network. This illustrates the efficacy of the method according to the invention to pattern in a highly site specific manner at a very small scale.

The thickness of the polymeric network patterned was evaluated by an optical profiler, and using the value for the refractive index as 1.465. Referring to FIG. 5 there is shown SEM images of the polymeric network pattered on to the silicon oxide substrate. To assist SEM imagery, the sample was first coated in gold (tilt 85°, accelerating voltage of 10 kV). SEM technology confirmed that the thickness of the polymer network on the biosensor substrate was 200 nm, as shown in FIG. 5(*b*).

Comparing this polymer thickness (200 nm) to the thickness described in the literature for an APTES monolayer (0.7 nm), it can be assumed that in terms of number of monolayers, the polymeric network is "ideally equivalent" to 286 monolayers of APTES. It will be appreciated that the polymeric structure cannot be over-simplified to a regular architecture composed of hundreds of monolayers covalently linked between them along a vertical axis. Nevertheless, the inventors believe that the determination of the polymer thickness is an important issue, since it proved the existence of a thick polymeric network patterning onto the silicon surface, which to date had never been achieved. This is a first condition required for substantiating a three-dimensional protein patterning. The inventors used techniques such as AFM, Confocal Microscopy and SEM to elucidate the structure of the polymeric network. From SEM and AFM pictures, the topography of the polymer surface suggested that its morphological structure is formed by the conglomeration of spherical polymer units, with dimensions from a few tens of nanometers to a few microns in diameter.

Referring to FIG. 6, there are shown SEM images of substrate of the biosensor. In FIG. 6(*a*), the sensor is not coated in gold (tilt 30°, accelerating voltage of 10 kV), and it is clear that relatively large spherical polysilane polymers are attached to a smoother polymeric background. At higher magnification, in FIGS. 6(*b*) and 6(*c*), it can be clearly seen that that the large spherical polymers are made up of smaller spheres of polymeric material cross-linked (covalently bonded) together. These observations fit well with the Atomic Force Micrograph picture shown in FIG. 7, where the individual polymer spheres can be seen.

In a preferred embodiment of methods of the invention, at the early stage of the polysilane polymerisation reaction, the polymerisation process takes place simultaneously at the silicon surface and also within the bulk of the solution. During the polymerisation reaction, nuclei or dots made from the bulk polymerisation start to covalently react with the surface polymer as their size continues to increase with time. Hence, the dots of polymer which are visibly attached to the surface of the substrate are formed. Despite the reaction mechanism being relatively difficult to control at the molecular level, two reasons make this "in situ" polymerisation process fully compatible with highly defined micro-features, for example, when immobilising biological molecules to the substrate of a biosensor. Firstly, the micron-size polymeric dots are easily removed from the polymeric background by ultra-sonicating the sample in the reaction solution for a few seconds. Secondly, the size of the polymeric dots, which react with the surface polymer to create the polymeric background, is controlled by the size and the shape of the photoresist mask.

The high resolution obtained with the 3 μm diameter circular features shown in FIG. 4(c) confirms the ability of the polymerisation process to fill the free space created in between the photoresist layer after photolithographic development, as shown in FIG. 1(a). Additional images were produced by Confocal Microscopy, where a polymeric network was created onto the whole clean surface of a glass slide. The thickness of the polymer was evaluated by imaging the vertical cross-section of the sample, and the value found to be around 8 microns. The micrograph shown in FIG. 8 reveals that the topography of this thick polymeric network has a filamentous structure. The inventors believe that this suggests that beyond a value of polymer thickness, the aggregation of polymeric dots formed in solution takes place along a vertical axis. Moreover, while the inventors do not wish to be bound by any hypothesis, they believe that the thickness of the polymeric network on the silicon surface may be dependent on the size of the photoresist patterning, due to physical constraints beyond a limit value of polymer thickness/surface ratio. For instance, if after the photolithographic steps, the exposed regions of the substrates are lines of 1 μm wide, then the polymer thickness obtained afterwards can be expected to be lower than if the lines are 100 μm wide.

In addition to immobilising biological molecules on silicon oxide substrates, the inventors have also shown that this polymeric network patterning may also be adaptable to other surfaces, such as gold. However, in such cases, the gold surface has to be initially modified with a self-assembled monolayer of aminated sulphur-containing molecule as cystamine. In a first step, the molecules of cystamine have to adsorb chemically onto the gold surface, in a highly self-assembled manner, exposing the primary amine groups towards the solution. Because they are highly nucleophilic, these primary amine groups can actuate in a similar way to the silanol groups contained at the silicon oxide surface, and react through a nucleophilic substitution with molecules of APTES, until the gold surface is entirely recovered with an APTES monolayer. Subsequently, the polymerisation of APTES monomers takes place at the substrate-solution interface, leading to the formation of an organosilane polymer on to the gold surface.

Example 3.3

Three-Dimensional Patterning of Biological Elements

The inventors have illustrated that it is possible to carry out three-dimensional patterning of biological elements with a polysilane polymer network on to a silicon substrate, and to absorb the biological molecules onto and into its structure. Several types of biological molecule have been successfully patterned onto the silicon surface following a procedure, which consists of covering the sample surface with a solution containing the biomolecule for a limited period of time before rinsing with water. The localization of absorbed and adsorbed biomolecule was followed by Fluorescent Microscopy using proteins conjugated with fluorescent labels.

Referring to FIG. 9, there is shown fluorescent micrographs of biomolecules adsorbed (a,b,c,d) into the polymeric network pattered on to the silicon substrate. As with other Figures, the patterning of the polysilane network is in the form of a MEMS biosensor platform, which has to be patterned with the biological element of interest. Highly defined protein patterns are shown in FIG. 9, where the efficiency of the silicon surface discrimination is proven by a non-existent background signal. Referring to FIGS. 9(b) and 9(d), the biological functionalization of the patterned area is directly visible since a fluorescent label was directly attached to the bioelement. Enzyme (FITC-HRP) was absorbed into the polysilane polymer structure. Both the enzyme (FITC-HRP) and the DNA probe (Rhodamine red DNA) are precisely located onto the silicon surface (which imitates the mass sensor platform) but no information about their remaining activity or selectivity.

In FIGS. 9(a) and (c), recognition specificity was given to the pattern by absorbing native antibodies (IgG) in to the polymeric network and then exposing the surface to the labelled antigen (FITC-anti IgG). Hence, the specific biological interaction antibody/antigen was made visible after incubation of the antibody modified sample into a fluorescein labelled antigen solution. In both cases, most of the fluorescent signal was due to the biological recognition process between antibody and antigen, with only a very minor contribution of non-specific adsorption of labeled antigen into the polymeric network.

Considering that prevention of non-specific adsorption is a major issue in any immuno-detection system, it became particularly important for the inventors to check the compatibility of this protein patterning technique with a routine immuno-assay procedure. The results obtained from this experiment, are shown in FIG. 10, which shows micrographs of patterned polymeric network modified with (1) no human IgG but FITC-anti-human IgG; (2) human IgG and then FITC-anti-rat IgG; and (3) human IgG and then FITC-anti-human IgG. The high specificity shown in FIG. 10(3) clearly shows that a standard procedure based on BSA blocking and detergent washing steps, is fully compatible with this protein patterning strategy, improving its biological selectivity.

A further experiment was carried out by the inventors to prove that in the same way as the antibodies of FIG. 10, the specificity of a DNA probe was maintained within the polysilane network. The results are shown in FIG. 11, where the fluorescent response due to the non-specific adsorption of non-complimentary FITC labelled DNA is very poor in comparison with the strong fluorescence obtained when the complimentary FITC labelled DNA hybridised with the absorbed probe. These results prove that a standard procedure for DNA hybridisation based on washing and blocking steps can be used to maintain the high specificity to the DNA probe coated polymer.

From the results shown and discussed above, the inventors believe that the biological molecule patterning procedure is sufficiently efficient to site-selectively immobilize biological molecules, at a micron scale, onto a silicon surface. Nevertheless, the fact that this biomolecule patterning takes place in a three-dimensional structure has been demonstrated by the use of a more powerful technique, as follows.

A glass slide was entirely modified with a thick polymeric network as discussed above, and left for incubation in a solution of fluorescein labelled antibody. In order to check how deep the protein was immobilized into the three-dimensional polymer structure (ie. penetration depth), the Confocal Microscopy technique was found by the inventors to be the more suited method. Referring to FIG. 12, there is shown a vertical cross-section of FITC-HRP absorbed into the polymeric network. As shown in FIG. 12, the vertical cross-section analysis (indicated by the x-z axis) revealed that the polymeric structure was fully loaded with the fluorescein labeled protein. Hence, with these experiments, the inventors have demonstrated their ability to create a biological three-dimensional structure, which can easily be patterned onto silicon surfaces.

Example 3.4

Comparative Study Between Three-Dimensional and Planar Protein Patterning

A number of known protein patterning strategies are based on the functionalization of selected regions of a silicon substrate surface by introducing aminosilanes, such as APTES, via standard "lift-off" procedures. However, in all of these prior art methods, the chemical discrimination only occurs adjacent and in the proximity of the silicon surface. Accordingly, the inventors refer to such methods as "planar protein patterning", or "2D", techniques. The prior art methods all set out to generate APTES monolayers on the silicon surface. Because of this reason, they all disclose the use of organic solvents, such as toluene, acetone, ethanol or methanol, with the very intention of preventing the ability of APTES to "polymerize vertically", i.e. away from the plane of the substrate. However, of these organic solvents used, the inventors of the present invention found that only toluene can be used in the three-dimensional protein patterning procedure. This is because the others all act as very good solvents for Novolac based photoresists, and would therefore immediately dissolve the photoresist mask patterned onto the silicon surface, thereby making the photolithography steps impossible.

Accordingly, the inventors decided to compare the thickness of APTES layers obtained with different toluene solutions with the thickness of the polymeric network generated when triethylamine (TEA) is used as organic solvent. In order to compare the three-dimensional patterning of biological material with standard "lift-off" protein patterning procedures also based on APTES chemistry (Wieringa, R. H. PhD Thesis, University of Groningen, December 2000, Chap 2; Weiping, Q. et al. J. Colloids & Interf. Sc. 1999, 214, 16-19; Weiping, Q. et al. Mat. Sc. & Engin. C 1999, 8-9, 475-480; Zhang, G. J. et al. Sens. Actuat.B 2004, 97, 243-248; Zang, C. X. et al. 8th International Conference on Electronic Materials (IUMRS-ICEM) 2002, Xi' an, China; Zheng, J. et al. Langmuir 2000, 16, 4409-4412; Britland, S. et al. Biotechnol. Prog. 1992, 8, 155-160; Wang, Z. H. et al. Colloids & Surfaces B 2004, 34, 173-177; Heiney, P. A. et al. Langmuir 2000, 16, 2651-2657), several chemical protocols were followed for silanizing the exposed silicon surface with APTES.

A series of identical photoresist patterned samples were treated, for 5 hours and at room temperature, with 2% APTES diluted in a) toluene; b) toluene containing 10% TEA; c) TEA. All the samples were sonicated in acetone for 5 min and dried under air stream. The thicknesses of APTES layers (whether polymerized or not) obtained from each solvent were then calculated with surface profiler measurements. The comparative study carried out with three different chemical solvents for the APTES silanization reaction was followed by incubating the samples in HRP-FITC solution (100 µg mL$^{-1}$, 1 hour, Room temperature) in order to compare the different APTES modified surfaces in terms of ability to adsorb/absorb proteins.

Referring to FIG. 13, there is shown micrographs of cross features of biosensors patterned onto silicon surfaces obtained by treating chemically a silicon surface coated with a photoresist mask with (a) 2% APTES in toluene; (b) 2% APTES in toluene containing 10% TEA; (c) 2% APTES in TEA. Referring to the micrographs of FIG. 13(a) or (b), there was no visible patterning when the APTES silanization reaction was carried out with pure toluene or a mixture of toluene/TEA (9:1, V/V), reflecting the absence of any thick polymer on the silicon surface. In the fluorescence micrographs of FIG. 13, the protein patterns obtained with toluene and toluene/TEA as solvent, were virtually indistinguishable from the background, resulting in a poorly defined patterning. However, in contrast, the result obtained when APTES is diluted in TEA revealed clearly how dramatically the three-dimensional protein patterning improved the amount of protein site-selectively immobilized, giving rise to a very high contrast between the patterned regions and the planar background, as shown in FIG. 13(c).

Referring to FIG. 14, there is shown a graph which indicates that APTES film thickness formed on to silicon surface depends on the solvent which is used during the silanisation reaction. The evaluation of APTES layers by surface profilometry confirmed that the thickness of the polymer network was 3 nm, 0 nm, and 192 nm for toluene, toluene/TEA and 100% TEA respectively, as shown in FIG. 14. This showed that TEA is the most suitable solvent for the polymerisation reaction.

When the different APTES patterned surfaces were incubated with a fluorescein labeled protein solution, the relationship between APTES thickness and the amount of protein adsorbed/absorbed became evident. Referring to FIG. 15, there is shown micrographs obtained after incubation of APTES patterned silicon oxide surfaces in a FITC-HRP solution. As described with reference to FIG. 13, APTES patterning was attempted using several chemical conditions: (a) 2% APTES in toluene; (b) 2% APTES in toluene containing 10% TEA; (c) 2% APTES in TEA. In the fluorescence micrographs of FIG. 15, the protein patterns obtained with toluene and toluene/TEA as solvent, were indistinguishable from the background, resulting in a very poorly defined patterning. However, in contrast, the result obtained when APTES is diluted in TEA revealed clearly how dramatically the three-dimensional protein patterning improved the amount of protein site-selectively immobilized, giving rise to a very high contrast between the patterned regions and the planar background, as shown in FIG. 15(c).

Example 3.4

Multi-Protein Patterning Methodology

The ability to pattern several proteins on selected regions of a silicon surface is a major issue for the rise of multi-analyte detection devices, such as biosensors. The most popular technique is currently the soft lithography technique based on micro-contact printing of proteins onto solid substrates. However, despite its success, the amount of protein physically adsorbed or covalently attached to the surface rarely exceeds one monolayer. As to protein patterning procedures based on conventional "lift-off" techniques, they face a serious problem when more than one protein has to be patterned on a same surface. This problem resides in the fact that the organic solvents and alkaline solutions used to develop and remove the photoresist are incompatible with most biological materials. Therefore, integration of biological elements into photolithographic processes remains a huge challenge.

Sorribas et al., discussed supra proposed a solution to the problem set by embedding the bioelement monolayer into a sucrose layer. With this procedure they successfully achieved a bi-biomolecular patterning. However, the feature drawn by the first protein was the negative of the second one, thereby dramatically limiting the versatility of the process. In this context, the three-dimensional protein patterning methods in accordance with the present invention represents a very efficient alternative. The methodology for the three-dimensional multi-protein patterning is shown in FIG. 2. As the whole patterning process is based on conventional resist lithography techniques, the key point of the method according to the invention is to avoid the intrinsic incompatibility between proteins and the clean-room environment. The aim therefore to insulate the biological molecule freshly absorbed into the polymeric network from the lithographic process by re-covering it with a polymeric which is able to act as a protective layer. The suitability of different polymers to protect the biological molecule from the process of lithography were not known.

The inventors surprisingly found that gelatin constituted a good candidate for two major reasons:—
  (i) this natural gel constituted by water-soluble polypeptides shows good film-forming properties and is easily removable just with warm water;
  (ii) from preliminary experiments, the spin-coated gelatin resulted in a homogeneous thin layer onto silicon.

Referring to FIG. 16, there is shown a surface profile of a thin gelatin layer spin-coated onto silicon, obtained with a Zygo Newview 5020 machine. After sputtering a thin layer of gold onto the sample in order to assist visualisation, the gelatin layer thickness was estimated by surface profilometry to be 216 µm thick.

In order to check the efficiency of gelatin as a protective layer, samples prepared with an antibody patterning were re-covered with a thin gelatin layer before they were exposed to acetone for 5 minutes. Then, the gelatin was removed, and the surface was blocked with BSA and the samples incubated in a fluorescein labeled antigen solution. The results are shown in FIG. 17. Referring to FIG. 17(b), there is shown that direct contact of the antibody patterned substrate with acetone irreversibly damages the structure of the antibodies, resulting in a dramatic lose of their activity. However, as shown in FIGS. 17(c) and (d), the gelatin layer successfully insulated the patterned antibodies from the organic solvent acetone, allowing the specific recognition binding to take place.

Accordingly, the inventors believe that this protective effect of a gelatin layer on the biological molecule absorbed/adsorbed on to the substrate, opens new possibilities for integrating the manipulation of biological materials in any conventional lithographic manufacturing process. For example, the combination of a gelatin protective layer with three-dimensional biomolecule patterning would give rise to a simple procedure for a multi-protein patterning, where all the stages take place in the clean-room. As a result, unlike methods in the prior art the number of different biological elements patterned on to a silicon surface using this methodology would be limited only by the resolution of the lithography technique and the surface area, and not the method of immobilisation as described above.

Example 4

Three Dimensional Patterning of Biological Element at a Nanometer Scale

Using the methodology described with reference to FIG. 1, a highly defined nano-scale biological patterning can be achieved. An e-beam patterned silicon die was provided by the National Centre of Microelectronics (CNM-Barcelona, Spain and was manufactured through a standard e-beam "lift-off" procedure using an electron beam sensitive resist material (polymethylmethacrylate (PMMA)) coated on to the silica. The die included a highly defined sentence with characters dimensions of 200 mm lines (see FIG. 19A).

The die was immersed in a 2% (v/v (solution of APTES in pure triethylamine for two hours at room temperature. The die was then dried under an air stream and sonicated in acetone in order to remove excess polymer and the photoresist. The patterned polymer was then cured at 120° C. for three hours. At this stage, the polymeric network was nano-patterned on the substrate surface with a very high definition (see FIG. 19B).

The die was then left to incubate in a FITC-labelled DNA solution (0.3 µM) for 30 min. and then washed with deionised water.

Using this procedure, a highly defined sentence has been "written" in DNA, with character dimensions of 200 nm lines (see FIG. 19C).

Conclusions

The three-dimensional biological molecule patterning methods in accordance with the invention brings valuable solutions to the serious problems and major limitations commonly found with conventional soft-lithography and "lift-off" based lithography techniques discussed above. In complete contrast with prior art techniques in which the chemical discrimination of silicon selective regions takes place only in the proximity of the substrate surface (i.e. 2D), the present invention generates a highly defined, three-dimensional network pattern, which extends away from the substrate surface, surrounded by a planar background.

The ability of the polymeric silane network to absorb biological molecules not only on to the surface thereof, but in addition, into and through its structure gives rise to a three-dimensional patterning. This increases the amount of biomolecule site-selectively immobilized by several orders of magnitude over the prior art methods. Moreover, the bound biomolecules retain their activity. The huge potential of the method according to the invention is due to its simplicity of use, robustness and versatility in terms of the variety of biological elements (enzymes, antibodies, cells or DNA), which can be potentially patterned on to a substrate surface. In addition, the immobilisation can be used with a diverse range of solid substrates (for example, silicon, glass and gold etc).

Furthermore, the method includes the deposition of a thin layer of gelatin onto the biological pattern, which acts as a protective layer from any chemical aggression during subsequent rounds of patterning. This simple procedure makes biological elements fully compatible with standard lithographic techniques routinely used in the clean-room environment. Finally, the ability to integrate bioelements within a lithographic process combined with the three-dimensional patterning approach has led to the design of a multi-protein patterning methodology, with a theoretically unlimited number of proteins immobilized at a micron scale.

The invention claimed is:

1. A method of immobilising a biological molecule, the method comprising:
  (i) covalently attaching a three-dimensional polysilane polymer to a substrate by subjecting the substrate to an in-situ polymerization reaction between organosilane monomers in an alkaline solvent; and
  (ii) attaching a biological molecule onto and within the polymer structure by one or more of absorption and adsorption.

2. A method according to claim 1, wherein the method comprises creating a polysilane polymer in selected 'target' regions of the substrate surface.

3. A method according to claim 1, wherein the substrate is first coated with a radiation sensitive material.

4. A method according to claim 3, wherein the radiation sensitive material includes a Novolac (TM) based photoresist layer.

5. A method according to claim 3, comprising curing the radiation sensitive material wherein curing is carried out by heating the substrate at a suitable temperature for a sufficient time.

6. A method according to claim 3, wherein target regions of the substrate on to which the biological molecule will be ultimately immobilized, are transferred to the radiation sensitive material covering the substrate by exposure to radiation.

7. A method according to claim 1, wherein the organosilane monomer has the following formula:

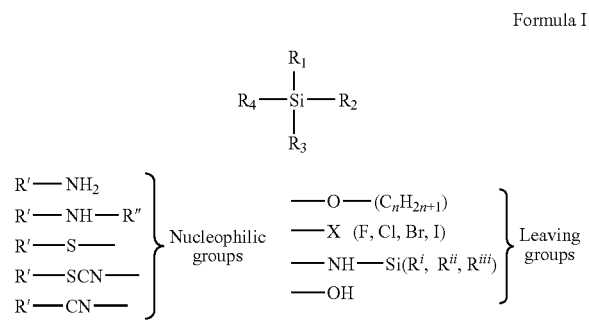

Formula I wherein at least one of $R_1$, $R_2$, $R_3$, and $R_4$ comprises at least one leaving group, and at least one of $R_1$, $R_2$, $R_3$, and $R_4$ is a nucleophilic group.

8. A method according to claim 1, wherein the polysilane polymer has been formed by the polymerisation of 3-aminopropyltriethoxysilane (APTES).

9. A method according to claim 1, wherein the solvent has a pKa which is higher than 8.

10. A method according to claim 1, wherein the solvent comprises triethylamine (TEA).

11. A method according to claim 1, wherein the substrate is dried, sonicated, and then cured.

12. A method according to claim 1, wherein the polysilane polymer comprises a plurality of silane molecules, which extend substantially along a plane of the substrate (2D) and substantially away from the plane of the substrate (3D), wherein the polysilane polymer is formed by first attaching silane molecules to the substrate, then covalently attaching a plurality of silane molecules to other silane molecules that are either directly or indirectly attached to the substrate.

13. A method according to claim 1, wherein the polymer is at least 150 nm thick.

14. A method according to claim 1, wherein step (ii) comprises incubating the substrate in a suitable buffer solution containing a suitable concentration of the biological molecule to be attached.

15. A method according to claim 14, wherein in step (ii) the biological molecule is absorbed and/or adsorbed onto and into the polysilane polymer produced by step (i) of the method.

16. A method according to claim 1, wherein the biological molecule comprises a nucleic acid molecule, amino acid, antibody, peptide, protein, enzyme, a whole cell, or part of a cell, a virus, phage, or a micro-organism, or an organelle, or a virus particle.

17. A method according to claim 1, wherein the substrate comprises any solid surface comprising glass or metal wherein the metal is selected from the group consisting of gold, silver, platinum, and palladium.

18. A method according to claim 1, wherein the substrate comprises silicon oxide.

19. A method according to claim 1, wherein the method comprises a step for pre-functionalising the substrate, prior to the step (i) of attaching the polysilane polymer thereto.

20. A method according to claim 19, wherein the pre-functionalising step is carried out either before or after the radiation sensitive material is applied.

21. A method according to claim 1 wherein, step (ii) of the method comprises attaching a plurality of different species of biological molecule to the polysilane polymer formed on the substrate.

22. A method according to claim 21, wherein the different species are attached to the substrate in discrete spaced-apart positions, or mixed together.

23. A method according to claim 21, wherein following step (i), the polymer is then coated with a chemically protective layer, which layer is adapted to protect the polymer from unwanted subsequent chemical treatment.

24. A method according to claim 23, wherein the chemically protective layer comprises gelatin.

25. A method according to claim 23, wherein the chemically protective layer is about 100 nm-500 nm thick.

26. A method according to claim 21, wherein the method comprises a step of coating the substrate or the chemically protective layer with a layer of radiation sensitive material.

27. A method according to claim 26, wherein when the radiation sensitive material covers the chemically protective layer, the substrate is then exposed to a source of radiation.

28. A method according to claim 27, wherein the substrate is incubated in the presence of a first species of biological molecule.

29. A method according to claim 28, wherein following attachment of the biological molecule to the polymer, the method comprises a step of coating the substrate with a chemically protective layer.

30. A method according to claim 29, wherein the substrate is exposed to radiation in order to remove selected target regions of the radiation sensitive material.

31. A method according to claim 30, wherein the substrate is incubated in the presence of a second species of biological molecule.

32. A method according to claim 31, wherein the second species of biological molecule is different from the first species of biological molecule.

33. A method according to claim 32, wherein by repeating the steps of patterning and attachment of biological molecules to the polysilane polymer 'n' times, 'n' different biological molecules are selectively attached onto the polymer on the substrate.

34. A method according to claim 33, wherein the method consists of removing any remaining radiation sensitive material, and any remaining chemically resistant material from the substrate.

35. A method according to claim 34, wherein the method comprises blocking the surface of the substrate with a suitable blocking agent in order to prevent non-specific protein adsorption/absorption.

36. A method according to claim 35, wherein the blocking agent comprises BSA in PBS.

37. A substrate comprising an immobilised biological molecule obtainable by the method according to claim 1.

38. A substrate according to claim 37, wherein the substrate is used as, or in the manufacture of, any device where it is necessary to functionalise a substrate surface of the device with a biological entity.

39. A device comprising a substrate obtainable by the method according to claim 1.

40. A device according to claim 39, wherein the device is a medical device, an implant, a bioreactor, a protein capsule, or a biosensor.

41. A method of manufacturing a biosensor comprising use of the method according to claim 1.

42. A method according to claim 41, wherein the biosensor is a MEMS biosensor.

43. A method according to claim 41, wherein the biosensor comprises a transducer, which is a mass resonator.

44. A method according to claim 41, wherein the biosensor is adapted to detect the presence of a biological target analyte, by measuring a frequency shift produced in the vibration modes of the circular disc resonator.

* * * * *